US012577524B1

(12) United States Patent
Viljoen et al.

(10) Patent No.: US 12,577,524 B1
(45) Date of Patent: Mar. 17, 2026

(54) MULTI-AXIAL MULTI-PORT EXTRUDER FOR CELL CULTURE

(71) Applicant: CellGro Technologies, LLC, Lincoln, NE (US)

(72) Inventors: Hendrik Jacobus Viljoen, Adams, NE (US); Jack Thomas Rauch, Lincoln, NE (US)

(73) Assignee: CellGro Technologies, LLC, Lincoln, NE (US)

( * ) Notice: Subject to any disclaimer, the term of this patent is extended or adjusted under 35 U.S.C. 154(b) by 575 days.

(21) Appl. No.: 18/163,545

(22) Filed: Feb. 2, 2023

Related U.S. Application Data

(60) Provisional application No. 63/306,549, filed on Feb. 4, 2022.

(51) Int. Cl.
| | |
|---|---|
| *C12M 1/00* | (2006.01) |
| *B29C 64/209* | (2017.01) |
| *B33Y 10/00* | (2015.01) |
| *B33Y 30/00* | (2015.01) |
| *B33Y 40/00* | (2020.01) |
| *C12M 1/32* | (2006.01) |

(52) U.S. Cl.
CPC .......... *C12M 47/02* (2013.01); *B29C 64/209* (2017.08); *B33Y 30/00* (2014.12); *B33Y 40/00* (2014.12); *C12M 23/40* (2013.01); *C12M 33/06* (2013.01); *B33Y 10/00* (2014.12)

(58) Field of Classification Search
None
See application file for complete search history.

(56) References Cited

U.S. PATENT DOCUMENTS

| | | | | |
|---|---|---|---|---|
| 4,072,457 A | * | 2/1978 | Cooksey | D01D 4/00 |
| | | | | 425/191 |
| 11,472,102 B2 | * | 10/2022 | Lewis | B33Y 10/00 |

(Continued)

OTHER PUBLICATIONS

Hsiao, A. et al., "Smooth Muscle-Like Tissue Constructs with Circumferentially Oriented Cells Formed by the Cell Fiber Technology," PLOS/ONE, Research Article, DOI:10.1371/journal.pone.0119010, Mar. 3, 2015.

(Continued)

*Primary Examiner* — Henry H Nguyen
(74) *Attorney, Agent, or Firm* — Advent, LLP; Daniel J. Honz

(57) ABSTRACT

Systems and methods for multi-axial multi-port extruders for producing multiple alginate tubes simultaneously are described. A system embodiment includes, but is not limited to, a plurality of input ports coupled with an extruder body, the extruder body defining a plurality of fluid channels, wherein each fluid channel is fluidically coupled with a respective one of the plurality of input ports, the extruder body further defining a plurality of branch portions including a plurality of branches extending from each fluid channel of the plurality of fluid channels; and a plurality of outlet ports fluidically coupled with the plurality of branches, wherein the number of branches extending from one fluid channel is equal to the number of outlet ports in the plurality of outlet ports to fluidically couple each input port of the plurality of input ports with each outlet port of the plurality of outlet ports.

16 Claims, 14 Drawing Sheets

(56) References Cited

U.S. PATENT DOCUMENTS

| | | | |
|---|---|---|---|
| 2011/0220498 A1* | 9/2011 | Ko | G01N 27/44791 |
| | | | 137/833 |
| 2021/0017485 A1* | 1/2021 | Lei | C12M 25/14 |
| 2021/0154916 A1* | 5/2021 | Kazmer | B33Y 30/00 |
| 2021/0370590 A1* | 12/2021 | Beyer | B29C 64/209 |
| 2023/0034642 A1* | 2/2023 | Chang | B29C 64/118 |

OTHER PUBLICATIONS

Nusterer, M. et al., "Theoretical and experimental investigation of alginate microtube extrusion for cell culture applications," Biochemical Engineering Journal, https://doi.org/10.1016/j.bej.2021.108236, Available online Oct. 14, 2021.

Onoe, H. et al., " Metre-long cell-laden microfibres exhibit tissue morphologies and functions," Nature Materials, vol. 12, DOI: 10.1038/NMAT3606, www.nature.com/naturematerials, Jun. 2013.

* cited by examiner

MULTI-AXIAL MULTI-PORT EXTRUDER FOR CELL CULTURE

CROSS-REFERENCE TO RELATED APPLICATIONS

The present application claims the benefit under 35 U.S.C. § 119 (e) of U.S. Patent Application Ser. No. 63/306, 549, filed Feb. 4, 2022, and titled "MULTI-AXIAL MULTI-PORT EXTRUDER FOR CELL CULTURE," which is herein incorporated by reference in its entirety.

FEDERALLY SPONSORED RESEARCH STATEMENT

This invention was made with government support under contract number 1R41GM134730 awarded by the National Institutes of Health. The government has certain rights in the invention.

BACKGROUND

Cell culture involves isolating cells for growth under controlled conditions and is an important process in bio-manufacturing, cell therapies, and cell biology. Cell therapies and regenerative medicine have high potential in treating many diseases, where cells proliferated by cell culture can provide direct therapies or can be modified for introduction into patients. Cells proliferated by cell culture can also serve as model systems for studying physiology and biochemistry of the cells or other diagnostic functions like disease models and drug screening.

SUMMARY

Systems and methods for providing multi-axial extruded cell culture systems with a plurality of output ports are described. A system embodiment includes, but is not limited to, a plurality of input ports coupled with an extruder body, the extruder body defining a plurality of fluid channels, wherein each fluid channel is fluidically coupled with a respective one of the plurality of input ports, the extruder body further defining a plurality of branches extending from each fluid channel of the plurality of fluid channels; and a plurality of outlet ports fluidically coupled with the plurality of branches, wherein the number of branches for extending from one fluid channel is equal to the number of outlet ports in the plurality of outlet ports.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. In the figures, the use of the same reference numbers in different instances in the description and the figures may indicate similar or identical items.

DETAILED DESCRIPTION

Overview

Figures 1A, 1B:
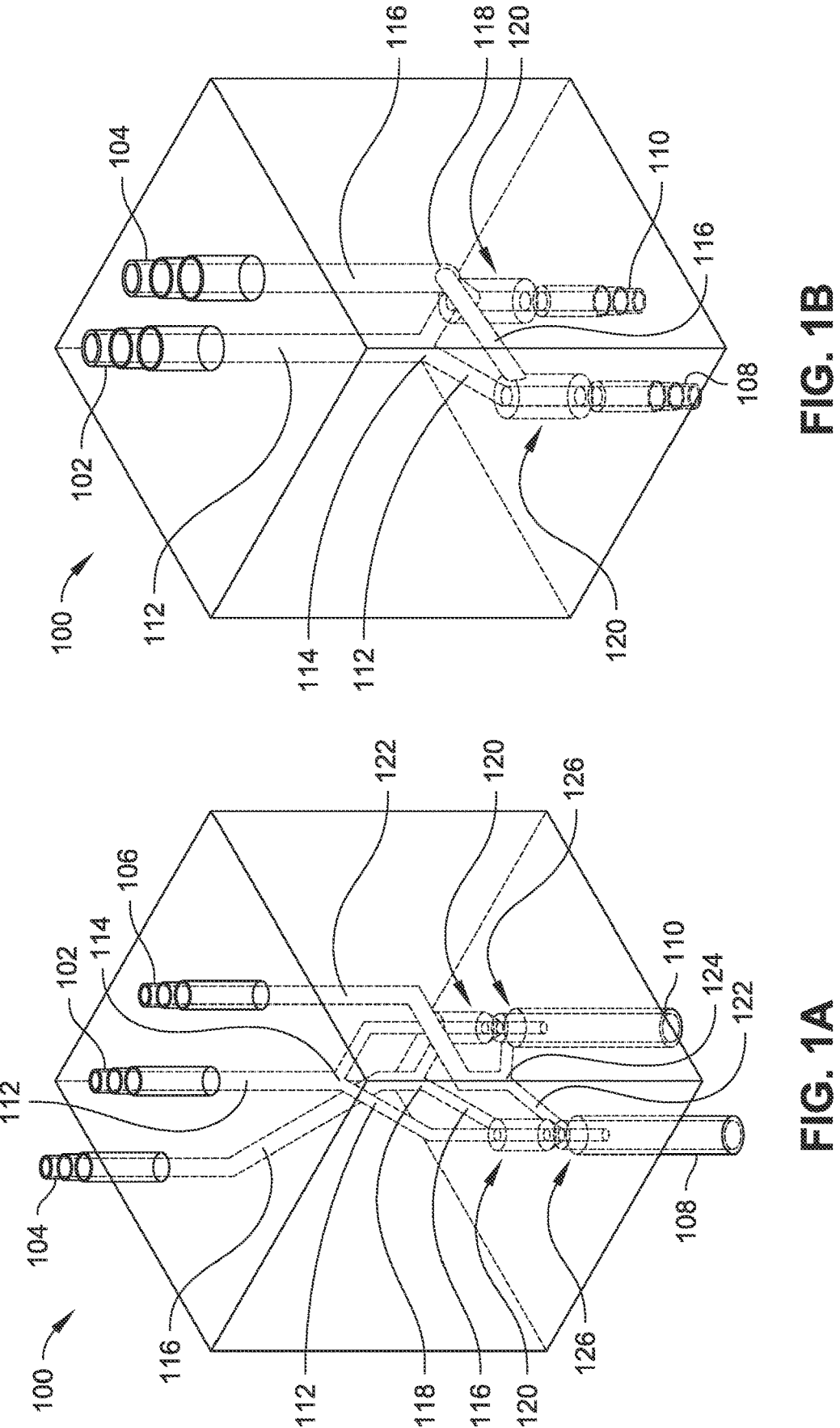
FIG. 1A is an isometric view of a tri-axial two-port extruder in accordance with example embodiments of the present disclosure.
FIG. 1B is an isometric view of a bi-axial two-port extruder in accordance with example embodiments of the present disclosure.

Cell culture technology enables production of cells used for treatment of diseases, clinical and laboratory research, and other life-changing uses. However, manufacturing cells on large scales to meet ever increasing demands of cells remains a challenge for a variety of reasons, including but not limited to, cell environment issues, issues associated with scaling up cell production, and issues scaling out cell production. For cell growth environments, stirred tank bioreactors can provide environments to culture cells, but such bioreactors do not provide cells with protection from hydrodynamic effects of the internal fluid environment of the bioreactor. Shear stresses in particular have a deleterious effect on the cells. Suspended cells grow as clusters. When the diameter of the cluster becomes too big, cells at the center of the cluster are deprived of nutrients and eventually die.

Scaling up issues are often experienced with stirred tank bioreactors. For example, when cells are produced in stirred tank bioreactors, the initial cell load is placed in a small tank, and then transferred to a larger one when the cells have reached capacity. These transfer steps are referred to as passages. Several passages between tanks may be required to produce larger amounts. Maintaining sterility during passaging adds significantly to process complexity and cost. A significant challenge is to maintain similar hydrodynamic conditions when cells are transferred from one tank to another. Thus, one option to scale cell production up is to design large tanks with similar hydrodynamic characteristics to smaller tanks. However, such a task is particularly formidable from a fluid dynamic standpoint.

Scaling out issues can be involved with manufacture of cells for a single user for cell therapy. Scale out is the process to produce a large number of individual doses. Genetically engineered chimeric-antigen-receptor T cells (CAR-T) for cell therapy is one example where manufacturing large amounts of individual doses has been limited. Even if the cell number may not be as large as in scale up applications, passaging may still be required, and complexity and costs are high.

Accordingly, the present disclosure is directed, at least in part, to systems and methods for multi-axial multi-port extruders for producing alginate tubes for generating high density cell cultures from each port for use with small-dimensioned bioreactors. In an aspect, hollow alginate tubes are extruded from each port, with typical inner diameters of $150\,\mu\text{m}$ to $800\,\mu\text{m}$ and wall thicknesses of $25\,\mu\text{m}$ to $100\,\mu\text{m}$. The hollow tubes are simultaneously seeded with cells in the hollow interior space. The alginate tubes shield cells from hydrodynamic forces which may exist outside the tubes. Initially, the alginate tubes from each port are simultaneously seeded at cell densities of 0.5 cells/mL to 10 million cells/mL. The alginate walls are permeable to nutrients and metabolites, thence cells grow in the hollow space until the cells completely fill the interior of the tube. Cell densities as high as 0.5 cells/mL to 1 billion cells/mL have been achieved.

During use of a tri-axial multi-port extruder, a first input port is coupled with a source of cell solution for pumping cell solution into the tri-axial multi-port extruder, a second input port is coupled with a source of hydrogel solution (e.g., sodium alginate solution) for hydrogel solution into the tri-axial multi-port extruder, and a third input port is coupled with a source of a cross-linking fluid (e.g., calcium chloride solution) for pumping cross-linking solution into the tri-axial multi-port extruder. In the extruder, the three flows combine in a co-axial arrangement, with the cell solution at the center, the hydrogel solution forming an annulus around the cell solution, and the cross-linking solution forming an external sheath around the hydrogel to cross link the hydrogel forming a stable tube with the cell solution in the interior.

During use of the bi-axial multi-port extruder, a first input port is coupled with a source of cell solution for pumping cell solution into the bi-axial multi-port extruder and a second input port is coupled with a source of sodium alginate solution for pumping sodium alginate solution into the bi-axial multi-port extruder. In the extruder, the two flows combine, with the cell solution at the center and the sodium alginate solution forming an annulus around the cell solution. The combined flow exits the tip of the extruder, which is positioned above or within a calcium chloride solution.

When the combined flow is introduced to the calcium chloride solution, the cross-linking reaction occurs to form a stable alginate tube with the cell solution in the interior. While the cross-linking reaction is rapid, the outflow of the combined flow from the extruder should avoid dispensing too quickly, otherwise the co-axial structure of the alginate and cell solution risks being destroyed before the cross-linking is complete. One potential issue during operation of the bi-axial multi-port extruder is the propensity of the exiting flow to clog around one of the extruder output port tips. When a tip clogs, the clog can be physically removed before efficient extrusion can continue. Stirring of the fluid can prevent or otherwise limit clogging by sweeping alginate tubes from the output port tips. However, in some instances of bioreactors, such stirring may be limited due to the closed structure of many bioreactor setups.

In an aspect, the high cell densities which are achieved in alginate tubes enable a drastic reduction in the size of the reactor that houses the alginate tubes. Compared to existing stirred tanks, the alginate tube reactor is at least about 50 to 100 times smaller, for equivalent cell production capacity. Further, the bioreactors used with embodiments of the present disclosure provide for single-container processing of the cells. For instance, in an aspect, once the alginate tube reactor is loaded, no further passaging is required. Cells remain in the same reactor for the duration of the culture period. The risk for contamination is less, and the cost savings are significant.

In an aspect, multi-axial multi-port extruders according to embodiments of the present disclosure include multiple input ports, where each input port is connected to an input channel that branches into two or more parallel flow channels. In implementations, the extruders include one parallel flow channel from each branch for each output port downstream from the branch. This configuration permits a given number of input channels to provide fluids to multiple output channels for a single extruder. Example extruder configurations include two input ports with two or more output ports (e.g., for bi-axial extruders) and three input ports with two or more output ports (e.g., for tri-axial extruders). Example extruders having 32 output ports for a set of two or three inputs ports can be manufactured according to implementations of the present disclosure. In an aspect, each of the parallel flow channels is coupled with an output port that can output the alginate tubes filled with cell solution. Bi-axial extruders can dispense the filled alginate tubes into a solution of calcium chloride to cross-link the alginate prior to transfer of the filled alginate tubes into a growth medium. Tri-axial extruders can include a port dedicated to a solution of calcium chloride to cross-link the alginate within each output port of the extruder nozzle or prior to introduction to a growth medium.

EXAMPLE IMPLEMENTATIONS

Figure 2A:
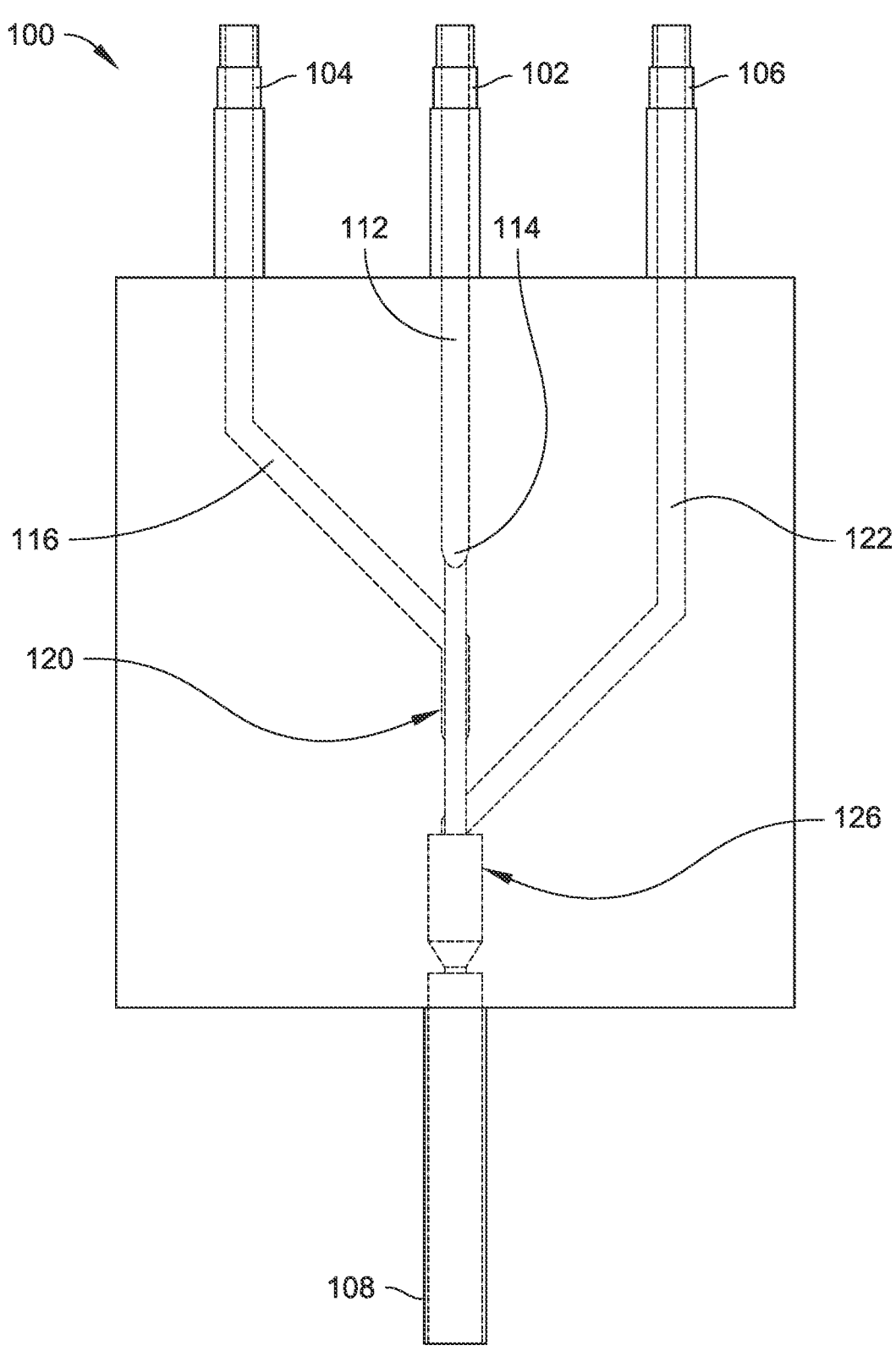
FIG. 2A is a side view of the tri-axial two-port extruder of FIG. 1A.
Figure 2B:
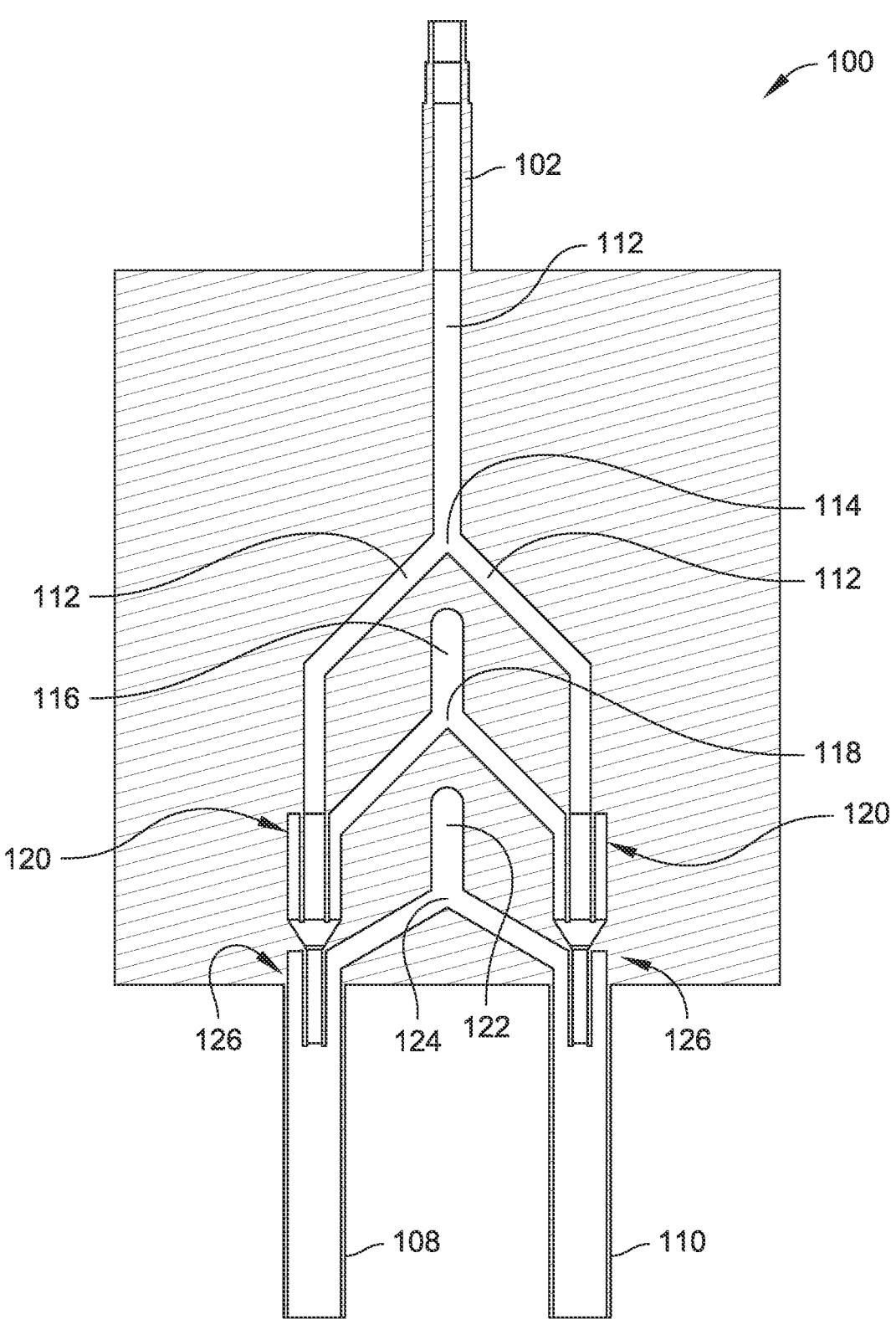
FIG. 2B is a cross sectional view of the tri-axial two-port extruder of the tri-axial two-port extruder of FIG. 1A.

Referring to FIGS. 1-9, aspects of multi-axial multi-port extruders configured to facilitate rapid production of multiple alginate tubes filled with cell solution in a simultaneous manner ("extruder 100") are shown in accordance with example embodiment of the present disclosure, with FIGS. 1A, 2A, and 2B illustrating examples of a tri-axial multi-port extruder and FIG. 1B illustrating an example bi-axial multi-port extruder. The extruder 100 is shown including two input ports (ports 102, 104) for a bi-axial multi-port extruder and three input ports for a tri-axial multi-port extruder (ports 102, 104, 106), with each extruder 100 shown having two output ports (ports 108, 110). While the extruders 100 are shown with two output ports, the present disclosure is not limited to extruders 100 having two output ports, where extruders 100 having more than two output ports can be provided without departing from the scope of the present disclosure. As examples, an extruder 100 having four output ports is shown in FIG. 5A and an extruder having eight output ports is shown in FIG. 5B, with corresponding scientific experiments having been conducted utilizing extruders 100 having greater than two output ports.

The input ports of the extruder 100 are configured to receive fluids to generate fluid-stable hydrogel tubes (e.g., alginate tubes) filled with a core of cell solution for introduction into a cell growth medium. For example, the port 102 is configured to receive a cell solution having cells for growth suspended in a fluid solution to facilitate transfer through the extruder 100. The port 102 is coupled with internal channels 112 of the extruder 100 to flow the cell solution through one or more branch portions 114 for distribution of the cell solution from a single input port to multiple outlet ports (e.g., ports 108, 110) in a co-axial arrangement with a hydrogel fluid (e.g., an alginate solution) and, in tri-axial extruders, with a fluid to cross-link the hydrogel (e.g., a calcium chloride solution). The branch portions 114 can include radial branches and planar branches and are described further herein with regard to FIGS. 4A through 5B. In implementations, the cell solution includes a cell density from about 0.5 million cells/mL to about 10 million cells/mL, however the present disclosure is not limited to such cell densities and can include cells densities less than about 0.5 million cells/mL or cell densities greater than about 10 million cells/mL without departing from the scope of the present disclosure.

The port 104 is configured to receive an alginate solution and direct the alginate solution through internal channels 116 of the extruder 100 to flow through one or more branch portions 118 for distribution of the hydrogel solution from a single input port to multiple outlet ports (e.g., ports 108, 110) in a co-axial arrangement with the hydrogel solution and, in tri-axial extruders, with the cross-linking solution. For example, the internal channels 116 and the branch portions 118 direct the hydrogel solution to two or more first chambers 120 wherein the hydrogel solution is prepared to flow around the flow of the cell solution in a co-axial arrangement to provide laminar, co-axial flows of the cell solution surrounded by the hydrogel solution. Example implementations of the first chambers 120 are described further herein with regard to FIG. 6. The internal channels 116 and the branch portions 118 are fluidically coupled with the port 104 and are independent of the internal channels 112 and branch portions 114 fluidically coupled with the port 102 to maintain separation of the cell solution and the hydrogel solution until they are flown past each other in the first chambers 120.

Figure 3:
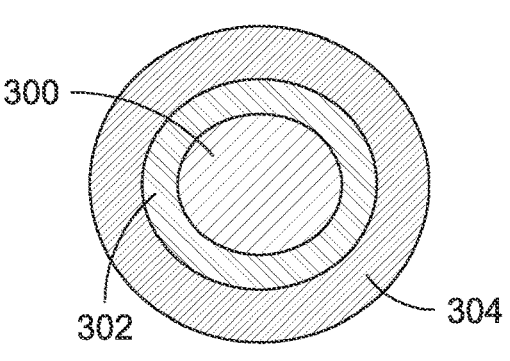
FIG. 3 is a diagrammatic illustration of a cross section of a product of one port of a tri-axial extruder, which can include a cell solution core, an alginate annulus, and a calcium chloride solution sheath.

For tri-axial extruders 100, the port 106 is configured to receive a cross-linking fluid (e.g., a calcium chloride solution) and direct the cross-linking fluid through internal channels 122 of the extruder 100 to flow through one or more branch portions 124 for distribution of the cross-linking fluid from a single input port to multiple outlet ports (e.g., ports 108, 110) in a co-axial arrangement with the hydrogel solution and the cell solution. For example, the internal channels 122 and the branch portions 124 direct the cross-linking fluid to two or more second chambers 126 wherein the cross-linking fluid is prepared to flow around the flow of the hydrogel fluid in a co-axial arrangement to provide laminar, co-axial flows of the cell solution surrounded by the hydrogel solution and the hydrogel fluid surround by the cross-linking fluid. Example implementations of the second chambers 126 are described further herein with regard to FIG. 6. The internal channels 122 and the branch portions 124 are fluidically coupled with the port 106 and are independent of the internal channels 112 and branch portions 114 fluidically coupled with the port 102 and independent of the internal channels 116 and branch portions 118 fluidically coupled with the port 104 to maintain separation of the hydrogel solution with the cell solution core until the cross-linking fluid is flown past the exterior of the hydrogel solution in the second chambers 126. For example, as shown in FIG. 3 the output from the outlet ports (e.g., ports 108, 110) can include a core 300 of cell solution surrounded by a layer 302 of hydrogel solution, which in axial extruders 100 is an annulus shape surrounded by a sheath 304 of cross-linking fluid to form hydrogel tubes containing cells within the interior for proliferation within a growth medium.

The branch portions of the extruders 100 are downstream of a substantially vertically-oriented internal channel, where the internal channel is diverted into two or more channels at the branch portion. A vertical orientation of the internal channel just before the branch portion and having substantially identical angles of channels coupled with the branch portion can reduce gravitational bias of fluid to be preferentially directed into one channel over another channel at the branch portion. By reducing the gravitational bias, the extruders 100 can have substantially equal flowrates of hydrogel tubes at the outlet ports, which provides hydrogel tubes having substantially equal dimensions. This control of flow rate can influence the growth of cells within the hydrogel tube interior by providing substantially similar growth effects of the cells (e.g., due to similar hydrogel wall thicknesses, similar cell core dimensions, etc.). If any one of the flow rates of cell solution, hydrogel solution, or cross-linking fluid preferentially flows through one channel following a branch portion, then the consistency of the product hydrogel tubes can be compromised. By providing even splits of flowrate through the internal channels following the branch portions, the extruders 100 can minimize variability of tube dimensions between the multiple outlets.

Figure 4A:
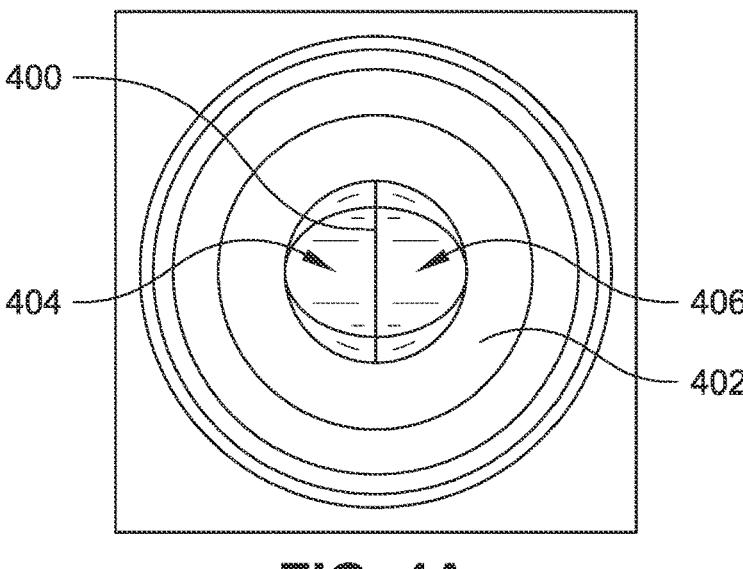
FIG. 4A is a top view of a branch region of a channel of an extruder splitting into two channels in accordance with example embodiments of the present disclosure.
Figure 4B:
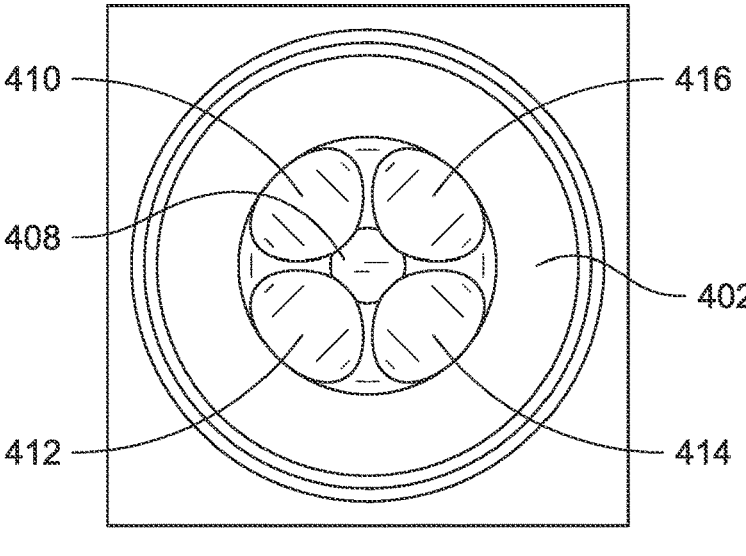
FIG. 4B is a top view of a branch region of a channel of an extruder splitting into four channels in accordance with example embodiments of the present disclosure.

Referring to FIGS. 4A through 5B, example configurations of branch portions (e.g., branch portions 114, 118, 124) are shown. In FIG. 4A, the branch portion is shown having an edge 400 that splits a vertical tube 402 (e.g., one of the internal channels 112, 116, 122) in half where two equal tubes 404, 406 extend from the vertical tube in opposite directions. In implementations, the tubes 404, 406 can extend from the vertical tube 402 at an angle from the horizontal from about zero degrees to about 85 degrees. For example, the tubes 404, 406 can extend from the vertical tube 402 at an angle from the horizontal from about 30 degrees to 60 degrees. In implementations, the tubes 404, 406 can extend from the vertical tube 402 at an angle from the horizontal of about 45 degrees. As the angle approaches 90 degrees from the horizontal, the split into separate tubes cause a longer duration for fluid separation, leading to increased dead volume and a taller footprint for the extruder. Additionally, as the angle approaches 90 degrees from the horizontal, the pressure drop and shear stress on the fluid decreases, particularly for the cell solution. In FIG. 4B, a radial branch portion is shown having a base 408 at a bottom of the vertical tube 402 with four tubes 410, 412, 414, 416 originating from the base 408 and extending in four different directions, such as when the extruder 100 is a four-outlet extruder. In implementations, the tubes 410, 412, 414, 416 can extend from the vertical tube 402 at an angle from the horizontal from about zero degrees to about 85 degrees. For example, the tubes 410, 412, 414, 416 can extend from the vertical tube 402 at an angle from the horizontal from about 30 degrees to 60 degrees. In implementations, the tubes 410, 412, 414, 416 can extend from the vertical tube 402 at an angle from the horizontal of about 45 degrees. The tubes 410, 412, 414, 416 can also be equally spaced relative to each other to limit preferential flow of flow to any one of the respective tubes. In implementations where the extruder 100 is formed from a resin printing process (e.g., stereolithography 3-D printing), the base 408 can be a flat base to provide structure to support the formation of the tubes 410, 412, 414, 416. For extruders 100 that include radial branch portions having differing number of extended tubes, different base configurations can be utilized, such as a rounded base, a pointed base, and so forth. While the radial branch is shown having four extending tubes, the radial branch can include any number of extending tubes to complement the number of output ports of the extruder 100.

Figure 5A:
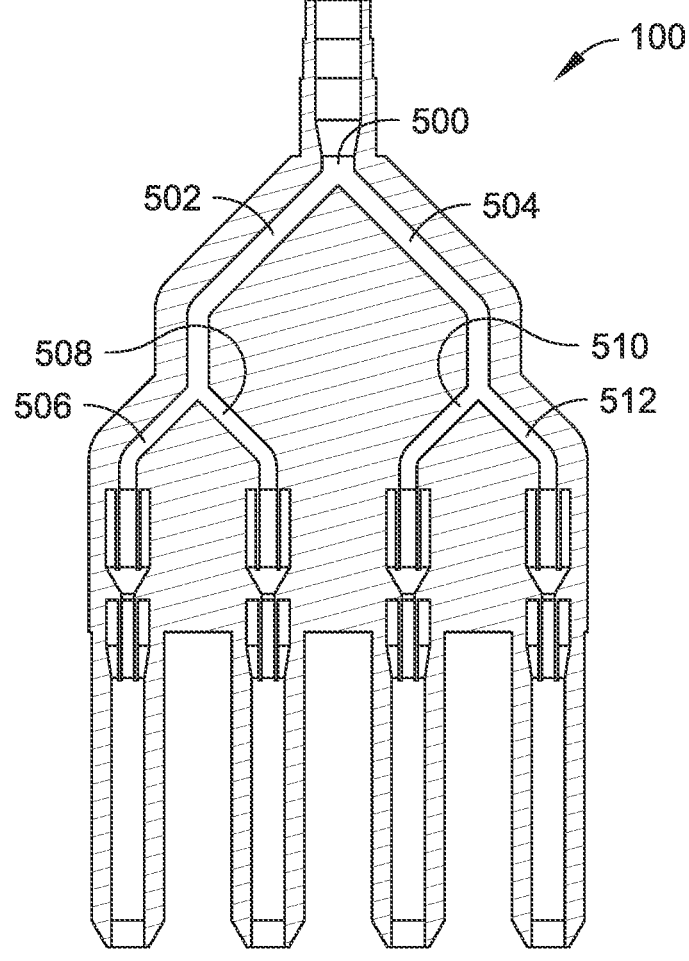
FIG. 5A is a cross-sectional view of a branch configuration of a multi-axial four-port extruder in accordance with example embodiments of the present disclosure.
Figure 5B:
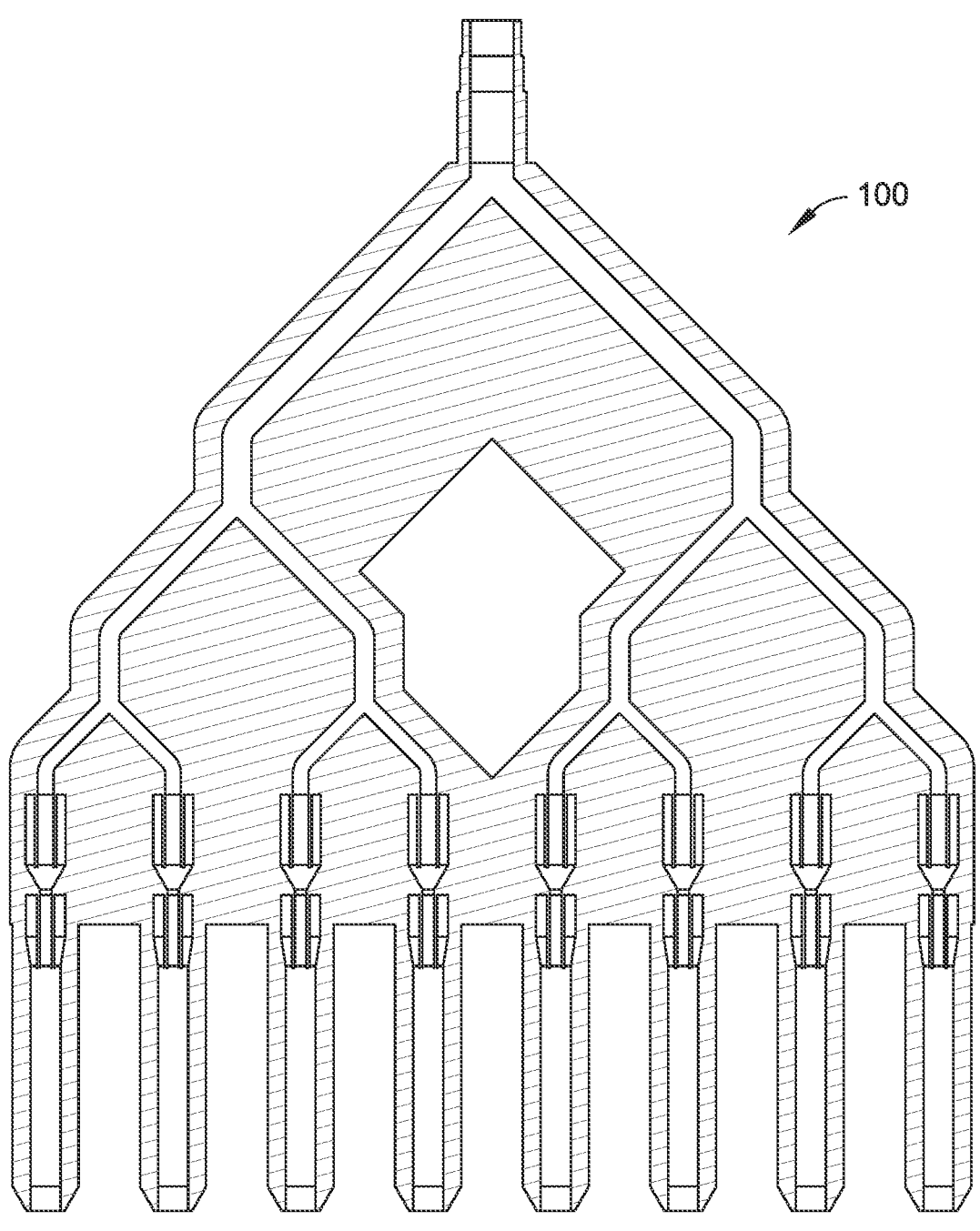
FIG. 5B is a cross-sectional view of a branch configuration of a multi-axial eight-port extruder in accordance with example embodiments of the present disclosure.

Referring to FIGS. 5A and 5B, example planar branch configurations of branch portions (e.g., branch portions 114, 118, 124) are shown. For an extruder 100 having two output ports, the branch points have a single split (e.g., as provided in FIG. 4A) to transfer flow from one internal channel to two internal channels. For extruder 100 having more than two output ports, the internal channels can include multiple portions where flow from one internal channel is split to two internal channels. For example, the extruder 100 shown in FIG. 5A includes branch portions having three splits to provide a four-outlet extruder, where channel 500 is first split into channels 502 and 504, where channel 502 is subsequently split into channels 506 and 508, and where channel 504 is split into channels 510 and 512. The extruder 100 shown in FIG. 5B includes branch portions having seven splits to provide an eight-outlet extruder. Each branch portion includes a split configured to avoid disrupting the laminar flow structure of the fluid flowing through the channels (e.g., the cell solution, the hydrogel solution, the cross-linking solution, etc.). For instance, sharp turns within the channels (e.g., 90 degree shifts) can be avoided to prevent disruption of laminar flow. Similarly, for the channels facilitating transfer of the cell solution, the channels avoid sharp turns to avoid excess shear stress on the cells. In implementations, the planar branch configurations utilizing 45 degree splits, where the channel from one split is directed to a substantially vertical orientation before the next split.

In general, the rate of tube generation from the extruder is dependent on the input flow rates, where the sum of the flow rate of the output ports is equal to the sum of the flow rate of the input ports (e.g., input ports 102, 104, 106). In implementations, a given branch portion is configured where the cross-sectional area of the substantially vertical channel is equal to the sum of the cross-sectional areas of the split channels. For example, for circular internal channels, a balanced cross-sectional equation is $\pi r_1^2 = n\pi r_2^2$, where $r_1$ is the radius of the substantially vertical channel, $r_2$ is the radius of one of the split channels, n=the number of split channels (e.g., for planar branch portions, n=2, for a four-port radial branch portion, n=4, etc.).

The extruders 100 can include structural features that facilitate laminar flows of the fluids through the internal channels and chambers that introduce the flow of one fluid around the exterior of another fluid (e.g., introducing the hydrogel solution around the cell solution, introducing the cross-linking fluid around the hydrogel solution, etc.). Such structures can prevent bubbles from forming in and around the chambers that introduce the flow of one fluid around the exterior of another fluid (e.g., the first chamber 120, the second chamber 126, etc.) to prevent the bubbles from introducing variations in hydrogel tube formation, hydrogel tube dimensions, and the like.

Figure 6:
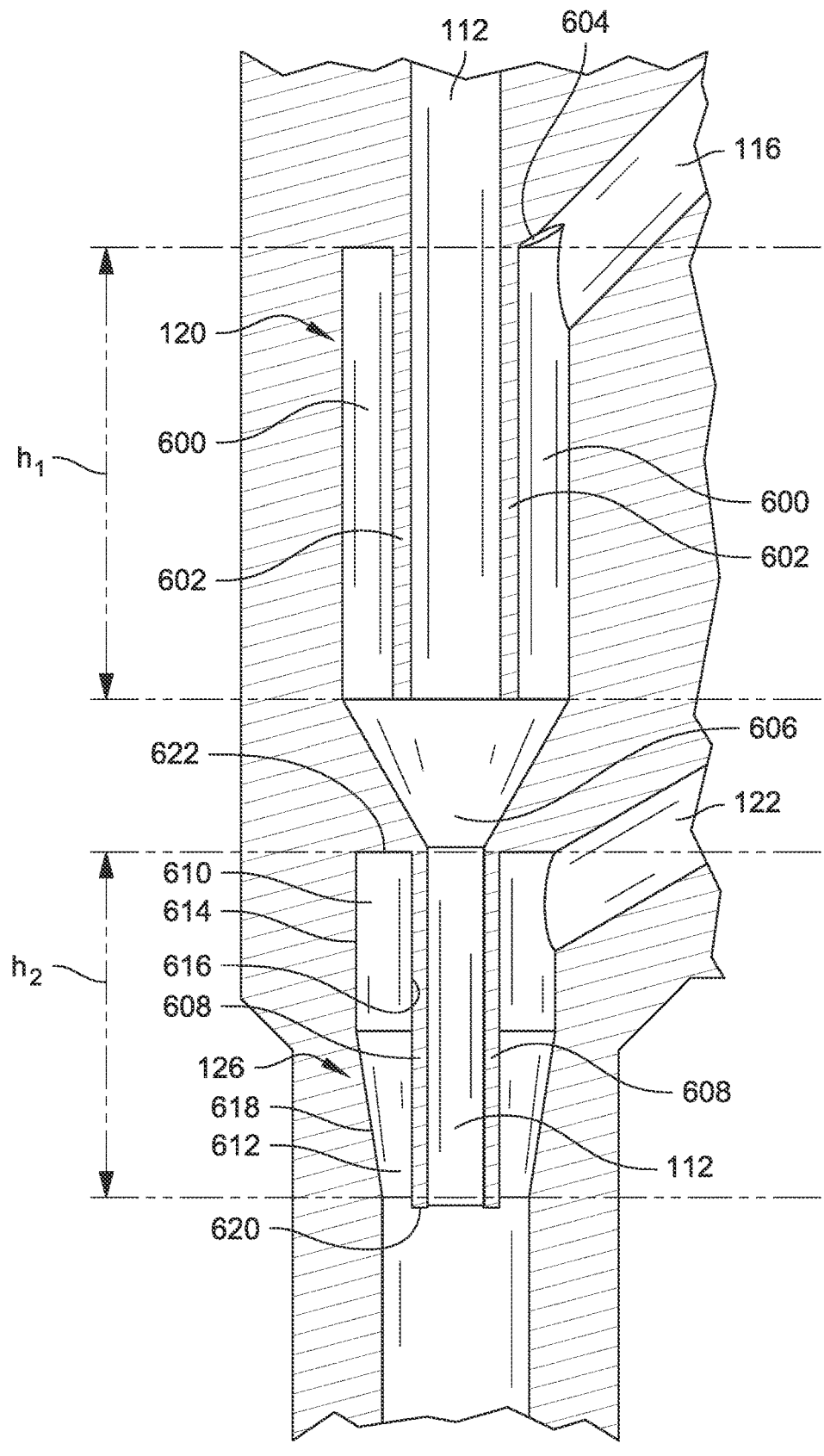
FIG. 6 is a partial cross-sectional view of a tri-axial extruder in accordance with example embodiments of the present disclosure.

For example, referring to FIG. 6, an example implementation of the first chamber 120 and the second chamber 126 is shown. The first chamber 120 directs the flow of hydrogel solution into an annular chamber 600 around the internal channel 112 to prepare a laminar flow of the hydrogel solution in a tube shape fully surrounding the cell solution that flows through internal channel 112. The first chamber 120 includes a separating wall 602 that separates the internal channel 112 from the annular chamber 600. In implementations, the separating wall 602 has a thickness from about 200 µm to about 300 µm to provide structural strength to prevent bending or warping of any particular region of the separating wall 602 relative to another region. For example, the separating wall 602 can be vertically oriented to center the flow of hydrogel solution into the annular chamber 600. If the separating wall 602 is too thin (e.g., for a resin-based material, less than about 200 µm), then the separating wall 602 could risk bending or warping in a direction during the fabrication process or in response to introduction of fluid flow into the annular chamber, resulting in uncentered fluid flow. While uncentered fluid flow could still result in formation of a hydrogel tube, a portion of the tube would have a smaller wall, which will reduce tube integrity by providing a potential point of structural failure.

In implementations, the first chamber 120 includes a fillet feature 604 at the intersection between the internal channel 116 and the annular chamber 600. The fillet feature 604 can assist the flow of the hydrogel solution to travel around the separating wall 602 to fully fill the annular chamber 600 when the extruder 100 is primed with fluid. For example, the fillet feature 604 aids the fluid flow in the transition from a circular cross section (e.g., in the internal channel 116) to the ring-shaped annular chamber 600, which reduces the likelihood that air would be entrapped in the chamber, particularly at the opposite side of the annular chamber 600 from where the internal channel intersects. The internal channel 116 can intersect the annular chamber 600 at a variety of angles. For example, the internal channel 116 can intersect the annular chamber 600 at an angle from the horizontal from about zero degrees to about 60 degrees. In general, the closer to a zero degree introduction (e.g., perpendicular to the annular chamber 600), the more likely that a laminar flow could be interrupted due to turbulence within the annular chamber 600, whereas the higher the angle, the more likely that air can form within the annular chamber 600 directly opposite from where the internal channel 116 intersects the annular chamber 600. In example implementations, the extruder 100 includes the internal channel 116 intersecting the annular chamber 600 at an angle from the horizontal from about 30 degrees to about 45 degrees.

In implementations, the separating wall 602 has substantially the same height (shown as $h_1$ in FIG. 6) around the annular chamber 600, where at least a portion of the fillet feature 604 is above the separating wall 602. For example, at least a portion of the fillet feature 604 extends above the top of the annular chamber 600 on the opposite side of the annular chamber 600 from the area where the internal chamber 116 intersects the annular chamber 600. In implementations, the annular chamber 600 has substantially vertical side walls for the entire height of the separating wall 602. For example, the annular chamber 600 can have a substantially vertical side wall, where the first chamber 120 includes a sloped base chamber 606 under the separating wall 602 that narrows the flow of the hydrogel solutions around and into contact with the cell solution. At this point, the hydrogel solution remains a liquid, since the cross-linking fluid has remained physically separate.

The second chamber 126 can also include a separating wall 608 to separate the combined flows of the hydrogel solution with the cell solution core and the separate cross-linking fluid. In implementations, the separating wall 608 separates an initial chamber portion 610 and a subsequent chamber portion 612 from the internal channel 112 that conveys the hydrogel solution with the cell solution core. The initial chamber portion 610 can have a substantially annular shape to initially receive the cross-linking fluid from the internal channel 122 into the second chamber 126 and direct the cross-linking fluid around the separating wall 608. The subsequent chamber portion 612 narrows in cross section prior to introduction of the cross-linking fluid to the hydrogel fluid stream to create more force of the cross-linking fluid to squeeze the exterior of the hydrogel fluid stream. In implementations, the initial chamber portion 610 has a distance between an outer wall 614 forming the exterior of the initial chamber portion 610 and an outer edge 616 of the separating wall 608 from about 700 μm to 1000 μm, whereas the subsequent chamber portion 612 includes a tapered wall 618 that narrows the distance to the separating wall 608 to about 400 μm to about 500 μm. For example, the tapered wall 618 can have a tapered angle from the horizontal from about 30 degrees to about 90 degrees. In general, the higher the angle, the lower the chance of introducing turbulence prior to introducing the cross-linking fluid to the laminar hydrogel fluid with the core of cell solution. In implementations, the tapered wall 618 has a tapered angle from the horizontal from about 70 degrees to about 88 degrees to reduce the change in cross sectional area and length, reducing a chance of a change in cross-sectional area introducing a low flow or dead zone or turbulence. For a 3-D printing construction technique, the tapered wall 618 facilitates printing the extruder 100 without a bridge being formed between the outer wall 614 or the tapered wall 618 and the separating wall 608. If a solid bridge were formed, then the presence of the bridge would disrupt the laminar flow of the cross-linking fluid and create an uneven flow around the separating wall 608.

In implementations, the second chamber 126 has substantially the same height (shown as h₂ in FIG. 6) around the internal channel 112 from a bottom 620 of the separating wall 608 to a top 622 of the initial chamber portion 610. The internal channel 122 can intersect the initial chamber portion 610 at a variety of angles. For example, the internal channel 122 can intersect the initial chamber portion 610 at an angle from the horizontal from about zero degrees to about 60 degrees. In general, the higher the angle of introduction of the cross-linking fluid to the initial chamber portion 610, the more likely that air can form within the initial chamber portion 610 directly opposite from where the internal channel 122 intersects the initial chamber portion 610. In example implementations, the extruder 100 includes the internal channel 122 intersecting the initial chamber portion 610 at an angle from the horizontal from about zero degrees to about 45 degrees.

Figures 7A, 7B, 7C:
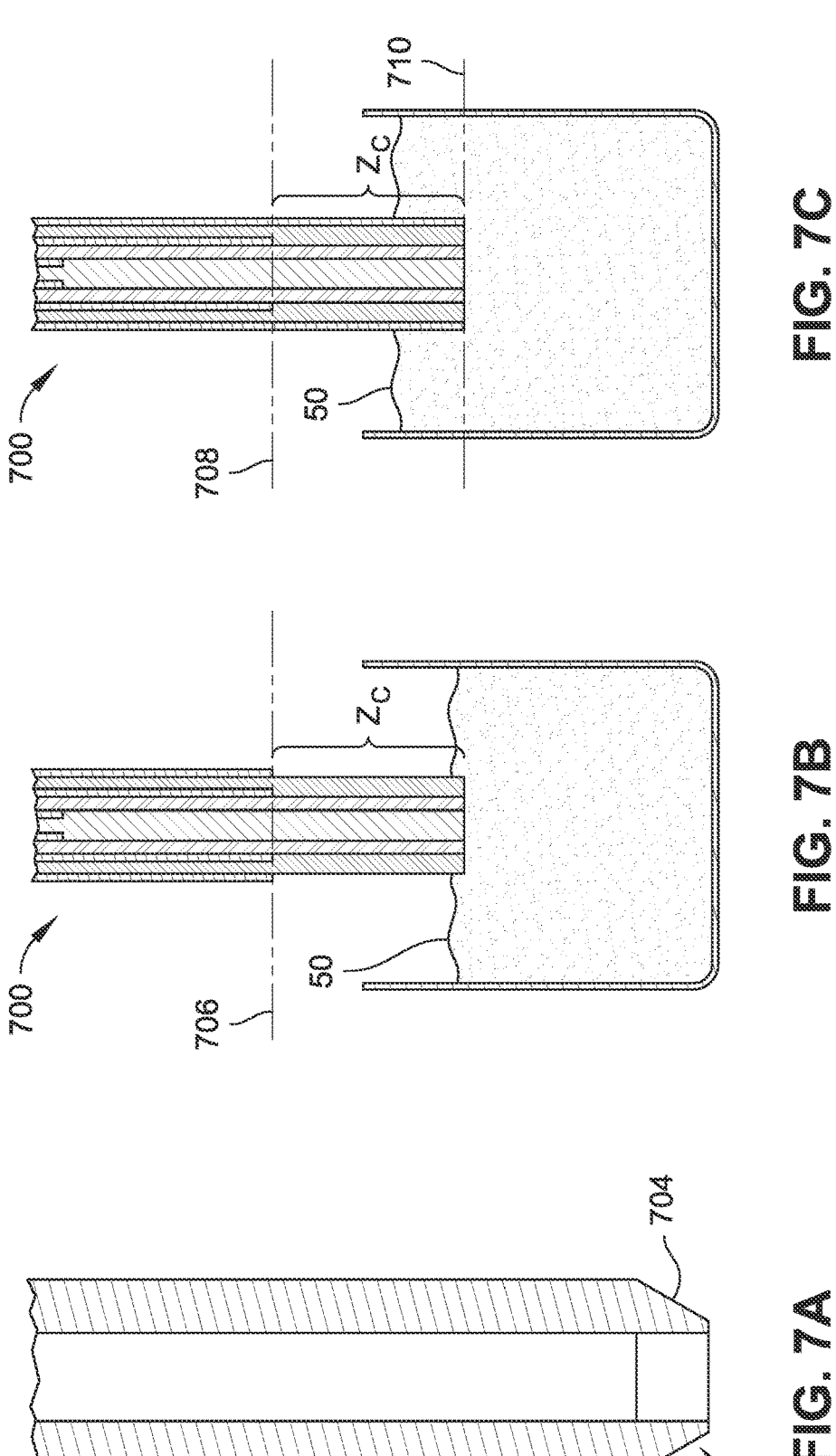
FIGS. 7A through 7C illustrate embodiments of an output port for a multi-axial extruder in accordance with example embodiments of the present disclosure.
Figure 8:
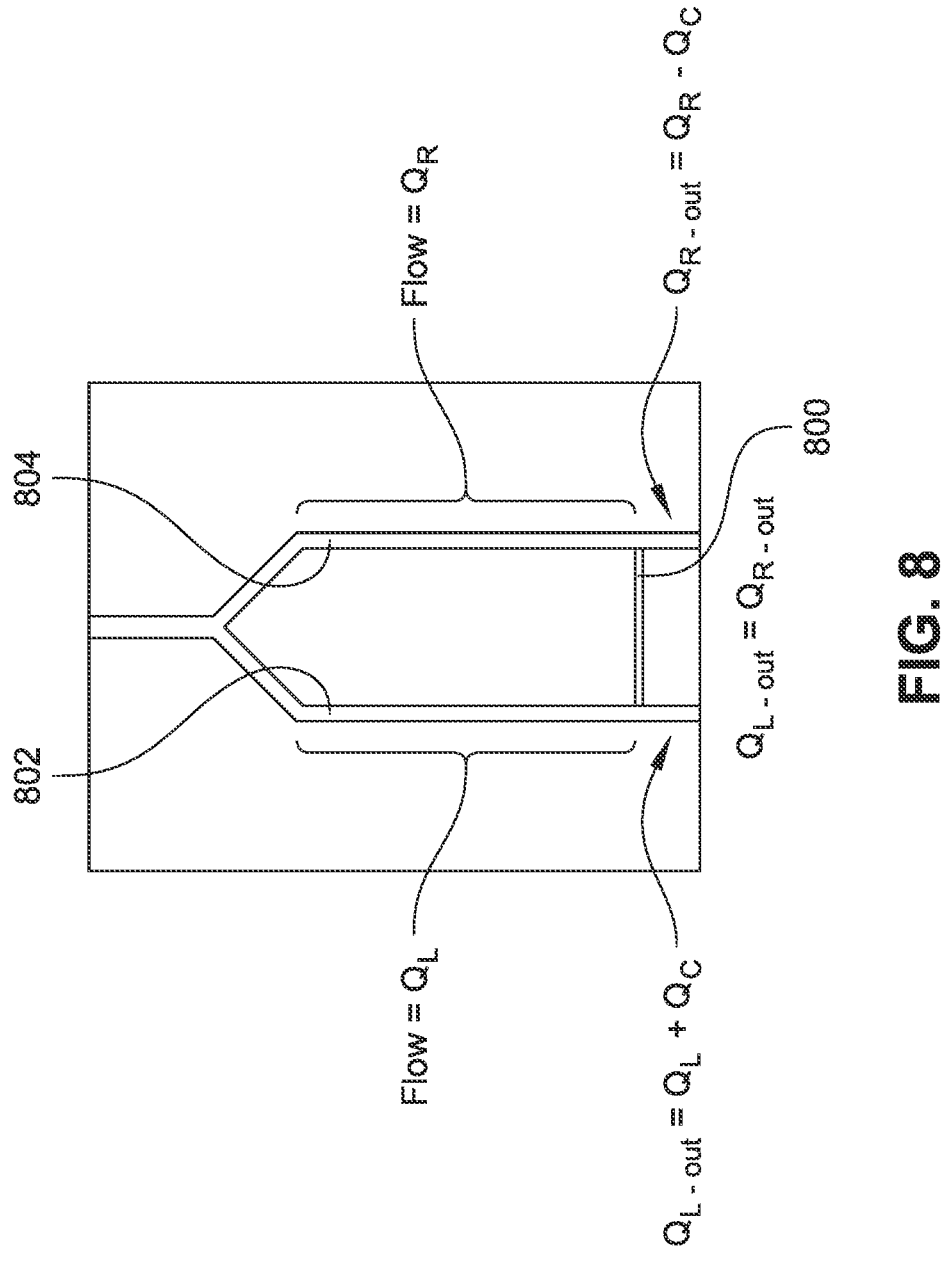
FIG. 8 is a schematic of a fluid flow channel splitting into two parallel channels with a connecting channel joining each of the parallel channels downstream from the split, in accordance with example embodiments of the present disclosure.

Referring to FIGS. 7A through 7C, aspects of the end of the outlet ports (e.g., ports 108, 110) of the extruder 100 are provided. In implementations, an example of which is shown in FIG. 7A, an outlet port 700 of the extruder 100 is shown having a tip 702 that includes sloped portions 704. For example, the sloped portions 704 can include a chamfered edge to reduce the thickness of the tip 702 relative to the remainder of the outlet port 700 while providing an interaction region that has reduced surface area that is perpendicular to the fluid into which the outlet port 700 is introduced during operation of the extruder 100. During operation, when the extruder 100 is inserted into the extrusion bath and the system is primed, air bubbles have a tendency to attach to flat areas at the bottom of the outlet port. For resin-printed construction of extruders, the resin used for these extruders is slightly hydrophobic which greatly increases the chances that a bubble will stick to this flat surface at the bottom of the outlet port. The bubbles are problematic since they disturb the flow of the cross-linked tube coming out of the extruder. The hydrogel tube can get pushed into the wall of the outlet port which results in complete disruption of the flow, the tube is not uniform and oftentimes the bubble causes the formation of a clog. For instance, even for hydrogel tubes that have been cross-linked due to exposure to the cross-linking fluid, the tube can still be linked to where the cross-linking fluid meets the hydrogel solution. Since the hydrogel becomes a solid, if the flow is disrupted downstream, the tube is still connected upstream to where the liquid to solid interface of the hydrogel is located. While flowing the cross-linking fluid or water at a high flowrate or a burst can help push the bubble out of the way, the bubble can float right back to where it was prior to being dislodged. The chamfer reduces the flat surface area at the tip 702 and hence the bubble is much weaker attached. Use of a chamfer has resulted in a dramatic reduction if not outright elimination of air trapped on/inside the nozzle tip 702. In implementations, the sloped portions 704 reduce the thickness of the tip 702 to a thickness from about 200 μm to about 300 μm. For example, the sloped portions 704 can have a chamfer angle of about 60 degrees to about 70 degrees from horizontal. If the angle increases further, the flat surface area is more reduced, but the structural integrity of the nozzle tip 702 becomes weaker, which can result in higher instances of breakage of the tip 702 (e.g., due to inadvertent contact between the tip 702 and the vessel in which the extruder 100 is introduced, etc.).

Referring to FIGS. 7B and 7C, two example output ports for a tri-axial multi-port extruder are shown. FIG. 7B shows a configuration where the output port 700 forms a needle having a structure with all portions terminating at the same distance (e.g., at tip edge 706). The output port 700 is held above the surface of the fluid 50 (e.g., cell growth medium) at a distance shown as z_c, to provide time for the sheath of calcium chloride to cross link the sodium alginate outside of the extruder 100 prior to introduction of the alginate tube to the fluid 50. In implementations, the distance z_c can be determined according to the methods described in *Theoretical and Experimental Investigation of Alginate Microtube Extension for Cell Culture Applications* by Nusterer et al. (Biochemical Engineering Journal 177 (2022) 108236), which is incorporated herein by reference in its entirety. FIG. 7C shows a configuration where the output port 700 forms a needle having a structure with an interior wall that terminates (e.g., at interior tip edge 708) prior to an exterior wall (e.g., at exterior tip edge 710) at the distance z_c, where such configuration can promote cross-linking of the alginate tube in the extruder 100, before the alginate tube enters into the fluid 50. In implementations, the fluid 50 can be a growth medium, which is more compatible with cells as compared to the case where the tubes are extruded directly into a calcium chloride (CaCl$_2$)) solution. Tri-axial extruders can also provide outlet ports that project the alginate away from the outlet port (e.g., the extruder tip 702) and into the fluid 50, preventing clogging of the port with alginate.

As described herein, the extruder 100 includes branch portions (e.g., branch portions 114, 118, 124) configured to evenly split the flow of incoming fluid to two or more internal fluid channels (e.g., channels 112, 116, 122), such as by structuring the incoming fluid channel as a substantially vertical channel and splitting the flow with substantially equal, parallel flows. To split a flow into parallel ones, with the requirement that each one of the parallel flow rates equals the other, is a very difficult problem to solve. The simplest case of a flow is a one channel that is split into two (e.g., a planar branch portion, such as shown in FIGS. 4A, 5A, 5B). For an incoming flow Q μL/min, the flow is split into a left branch flow (Q$_L$) and a right branch flow (Q$_R$). The two parallel lines are of equal length, L (mm), but the average diameters differ slightly, D$_R$=D$_L$+δ (e.g., due to imprecision in the diameter of the internal channel, caused by imperfect manufacturing techniques). At the outlet of the parallel lines, the pressure is the same. Thus, the pressure drop across each parallel line must be the same. Since the flows are laminar, the pressure drop is represented by equation 1:

$$\Delta P_L = \frac{128 \ \mu L \times Q_L}{\pi D_L^4} = \Delta P_R = \frac{128 \ \mu L \times Q_R}{\pi D_R^4} \qquad (1)$$

The flow through the right line differs from the flow through the left line according to equation (2):

$$Q_R = \left( \frac{D_L + \delta}{D_L} \right)^4 Q_R \qquad (2)$$

Different manufacturing techniques offer varying degrees of accuracy. For example, for 3-D printing, when the accuracy of the 3-D printer increases, the time to print an extruder typically increases. To commercialize extruders which are manufactured by 3-D printing, high precision printing is preferred, but at the same time relatively short processing times is desirable. In implementations, multi-axial multi-port extruders provided in accordance with example embodiments of the present disclosure are included with a horizontal connecting channel to connect two parallel channels. An example is shown with reference to FIG. 8, where a horizontal channel 800 connects the two parallel lines (802, 804) at a distance L$_F$=(5–10)×D$_L$ from the outlets. In implementations, L>100D$_L$, so the connecting channel is close to the outlet. The diameter of the connecting channel is D$_C$ and the length of the connecting channel is L$_C$. Inequalities in the flow resistance will cause a pressure difference across the connecting channel and there will be a flow from one parallel line to the other. The amount of flow in the connecting channel will correct for flow inequalities which occur between the point where the parallel start, and the point where they connect to the connecting channel (length L–L$_F$). Since the remaining (equal) lengths of the parallel lines are short (L$_F$), little discrepancies occur, and the flows are equalized. Denote the length above the connecting point L–L$_F$=L$_{top}$. The pressure drops in the left and right lines over L$_{top}$ are provided according to equations (3) and (4):

$$\Delta P_{Ltop} = \frac{128 \ \mu L_{top} \times Q_L}{\pi D_L^4} \qquad (3)$$

$$\Delta P_{Rtop} = \frac{128 \ \mu L \times Q_R}{\pi D_R^4} \qquad (4)$$

If D$_R$ is slightly larger, then $\Delta P_{Ltop} > \Delta P_{Rtop}$. If the pressure at the top, where the two lines split, is P, then the pressure at the right side of the connecting channel is larger than the pressure at the left connecting point, where P–$\Delta P_{Rtop}$>P–$\Delta P_{Ltop}$. And a flow Q$_C$ will flow from right to left, according to equation (5):

$$Q_C = \frac{[\Delta P_{Ltop} - \Delta P_{Rtop}]D_C^4}{128 \ \mu L_C} \qquad (5)$$

The exiting flow on the left is provided according to equation (6):

$$Q_{L\text{-}out} = Q_L + Q_C \qquad (6)$$

And the exiting flow on the right is provided according to equation (7):

$$Q_{R\text{-}out} = Q_R - Q_C \qquad (7)$$

In implementations of the present disclosure, the multi-axial multi-port extruders are printed within a biocompatible resin material. Non-biocompatible resins can result in seepage of the resin material into the flows of sodium alginate, cell solution, or calcium chloride can cause contamination of the alginate tubes and cell death.

Figure 9:
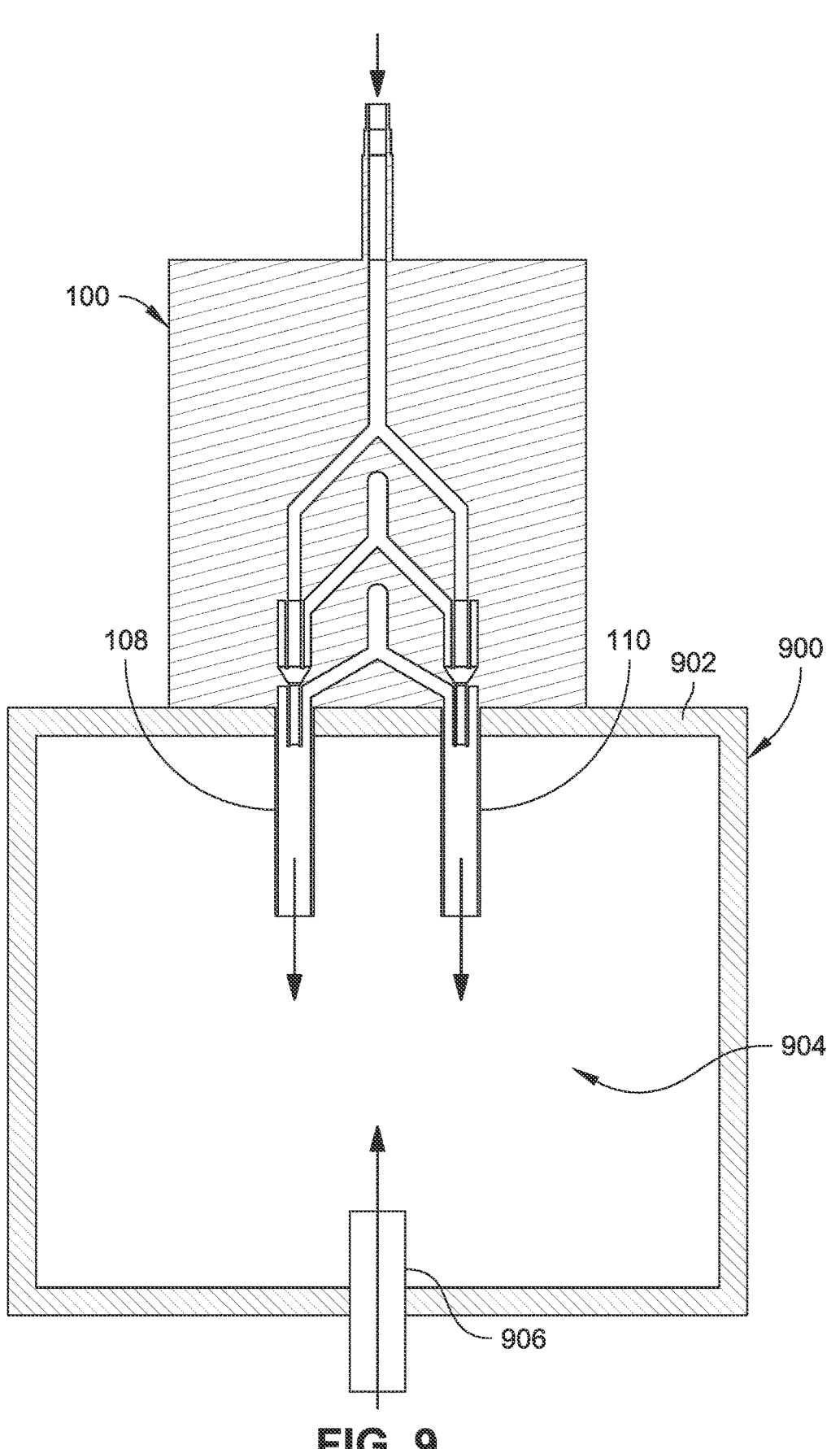
FIG. 9 is a cross-sectional view of a personalized bioreactor (PBR) coupled with a multi-axial multi-port extruder in accordance with example embodiments of the present disclosure.

The extruders 100 described herein (e.g., tri-axial multi-port extruder, bi-axial multi-port extruder) can be utilized with an alginate tube reactor for preparing single doses of cells for individual use, referred to as a personalized bioreactor or PBR, an example of which is shown in FIG. 9. The PBR 900 is shown including a tri-axial multi-port extruder 100 coupled to or integrated with a top portion 902 (e.g., a lid) of the PBR 900 such that the outlets 108 and 110 extend into an interior region 904 of the PBR 900 to introduce the alginate tubes into cell growth medium held within the interior region 904. An inlet 906 can introduce air bubbles to aerate the fluid within the interior region 904, which can suspend the alginate tubes within the PBR 900 to promote cell growth within the alginate tubes.

One aspect of including an extruder 100 in the PBR 900 is that the system can operate closed, without risk of contamination due to outside exposure. The alginate tubes, seeded with cells, are made in the PBR 900. The cells are placed in a stable cell solution before they are extruded into the alginate tubes. The cells are briefly exposed to shear stress during the extrusion process. The cells are kept in a container of cell solution, and from there are pumped through the extruder 100 into the PBR 900, where they are positioned inside the alginate tubes. An example comparison of a conventional stirred tank reactor and an alginate tube reactor configured as a PBR according to embodiments of the present disclosure is provided in Table 1:

TABLE 1

|  | Stirred Tank | Alginate Tube Reactor |
| --- | --- | --- |
| Starting number of cells | 10 million | 10 million |
| Final number of cells | 100 billion | 200 billion |
| Number of passages | 8 | 0 |

TABLE 1-continued

| | Stirred Tank | Alginate Tube Reactor |
|---|---|---|
| Culture period (days) | 40 | 20 |
| Bioreactor volume (L) | 1350 | 40-80 |

In implementations, it takes about 20 seconds for a cell to travel from the cell solution container until it ends up in an alginate tube (also referred to as the processing time $t_p$). A sodium alginate solution (1 to 2% w/v) can be used to form the alginate tube. In implementations, the sodium alginate solution is brought in contact with a 100 mM solution of $CaCl_2$). The $Ca^{2+}$ crosslinks the alginate to form a polymer. During the extrusion process, tubes which have been already made via the extruder, are exposed to the $CaCl_2$) solution and the cell solution. The $CaCl_2$) solution does not provide a stable environment for long time exposure to cells. For instance, extrusion processes that expose the tubes to calcium chloride in excess of 30 minutes greatly risk the viability of cells, for example, due to the tendency of calcium chloride displacing most of the growth medium from inside the tube by diffusion.

Given this window within which cells can be extruded, it is important to have an extruder with multiple extruder ports to provide parallel processing of multiple alginate tubes for a given input of alginate and cell solution into the extruder. In implementations, an upper limit on the rate at which the cells can be pumped through the extruder can be experienced; although the processing time $t_p$ will shorten, the shear stress will be higher. Another limit on the flow rates is the stability of the co-axial flows of fluids input into the extruder (e.g., alginate fluid, cell solution, and for tri-axial extruders, calcium chloride or other cross-linking fluid). The laminar co-axial structure of the combined flow of cell solution at the center, surrounded by the sodium alginate solution, is destabilized when flow rates are too large. Moreover, the internal diameter of the alginate tubes is generally limited by the ability of growth medium to diffuse across the alginate tubes and into the center of the tube to supply nutrients for cell growth and stability to cells located at or near the center. For a single output port extruder, it is estimated that a single extruder can produce about 2 mL of tube (via the inner tube volume) in the 30 minute period. Extruders having multiple output ports, as described herein, can therefore provide increased scalability while maintaining suitable flow characteristics to form and maintain the proper growth environment of the cells within the alginate tubes.

Example Experimentation of the Multi-Axial Multi-Port Extruders

Example 1-Tube-to-Tube Variability

Extruders 100 having differing output port numbers and branch portion configurations were analyzed to determine variations in physical dimensions of the individual tubes generated by individual output ports from the extruders 100 (e.g., tube-to-tube variability). Alginate tube samples from each individual nozzle were collected for measurement for each extruder 100, where the extruder designs included an extruder having two outlet ports (i.e., a 2-Port extruder), an extruder having four outlet ports and having radial branch portions (i.e., a 4-Port Radial extruder), an extruder having four outlet ports and having planar branch portions (i.e., a 4-Port Planar extruder), an extruder having eight outlet ports and having radial branch portions (i.e., an 8-Port Radial extruder), and an extruder having eight outlet ports and having planar branch portions (i.e., an 8-Port Planar extruder). The alginate tubes were introduced to a container having a custom-made separator that divided the container into individual baths for each outlet port to separate tubes from respective outlet ports.

For the 2-Port, 4-Port Radial, and 8-Port Radial extruders, the flowrates used were 40, 60, 10,000 uL/min/port for the core, shell, and sheath respectively. For the 4-Port Planar and 8-Port Planar Extruders, the flowrates used were 40, 60, 5,000 uL/min/port for the core, shell, and sheath respectively. The fluids for the core, shell, and sheath flows were 1.5% Methylcellulose (a viscosity of about 130 mPa*s), 2.0% Alginate (about 570 mPa*s) and 100 mM $CaCl_2$) (about 1 mPa*s).

The number of tubes collected from each port was three. Each tube was imaged five times. The average tube dimensions for each test were attained from averaging over the five pictures. The average dimensions and standard deviations for the tubes graphed were obtained from averaging the average dimensions over the three tests.

In every graph shown herein, the data shown is the average with error bars showing 1 standard deviation. The AVG bar on each graph is taking the average dimensions for each tube and averaging them as well as graphing the standard deviation in error bar form. Range is defined as the maximum minus the minimum average tube value.

Figure 10:
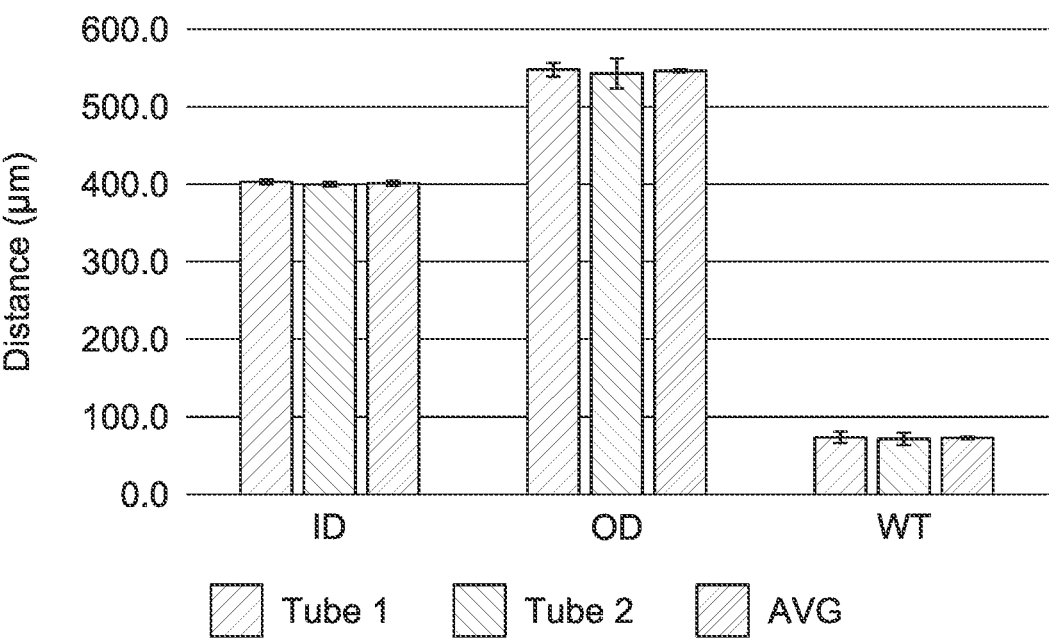
FIG. 10 is a chart illustrating alginate tube dimensions generated from a two-port extruder in accordance with example embodiments of the present disclosure.

Referring to FIG. 10, results of the analysis of the 2-Port extruder are shown, where ID is the inner diameter, OD is the outer diameter of the tube, and WT is the average wall thickness in each tube. The 2-Port Extruder is the simplest in terms of splitting flow. Each flow is only split once and then flow into their respective chamber and then forms tubes. The tubes demonstrated high reproducibility with very little deviation from the average, the highest being Tube 2 OD. The tubes were almost identical, with the AVG ID, OD, and WT having a standard deviation of 1.90, 2.37, and 1.55 μm respectively. The ranges for the ID, OD, and WT are 3.8, 4.7, and 3.1 μm respectively.

Figure 11A:
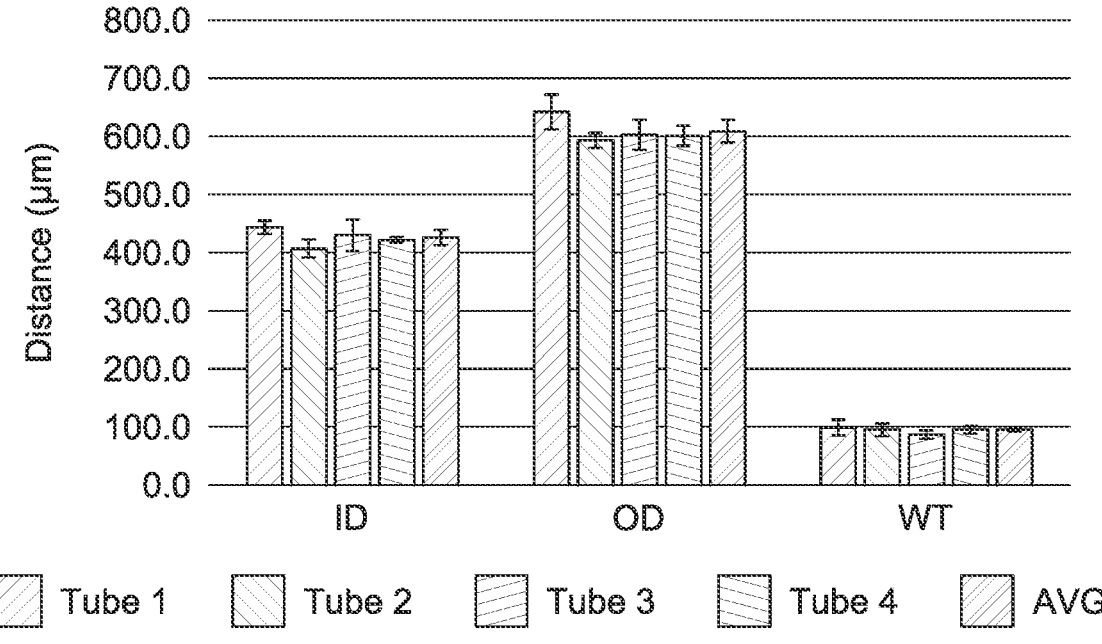
FIG. 11A is a chart illustrating alginate tube dimensions generated from a four-port radial extruder in accordance with example embodiments of the present disclosure.

Referring to FIG. 11A, results of the analysis of the 4-Port Radial extruder are shown. While the tubes demonstrated high reproducibility, the splitting was not observed to be as even as from the 2-Port extruder. Without being held to a particular theory, it is believed that the drop in split equality of the flow is due to the geometry of the radial branch portion shown in FIG. 4B, where the flat base 408 creates a stagnation plane onto which the incoming flow collides, which destabilizes the flow and causes an uneven distribution between the four exiting flows. Here the AVG standard deviations for ID, OD, and WT are 13.4, 19.7, and 4.5 μm respectively. The range of ID, OD, and WT are 36.8, 51.2, and 12.5 μm respectively, which is an order of magnitude larger than the 2-Port results.

Figure 11B:
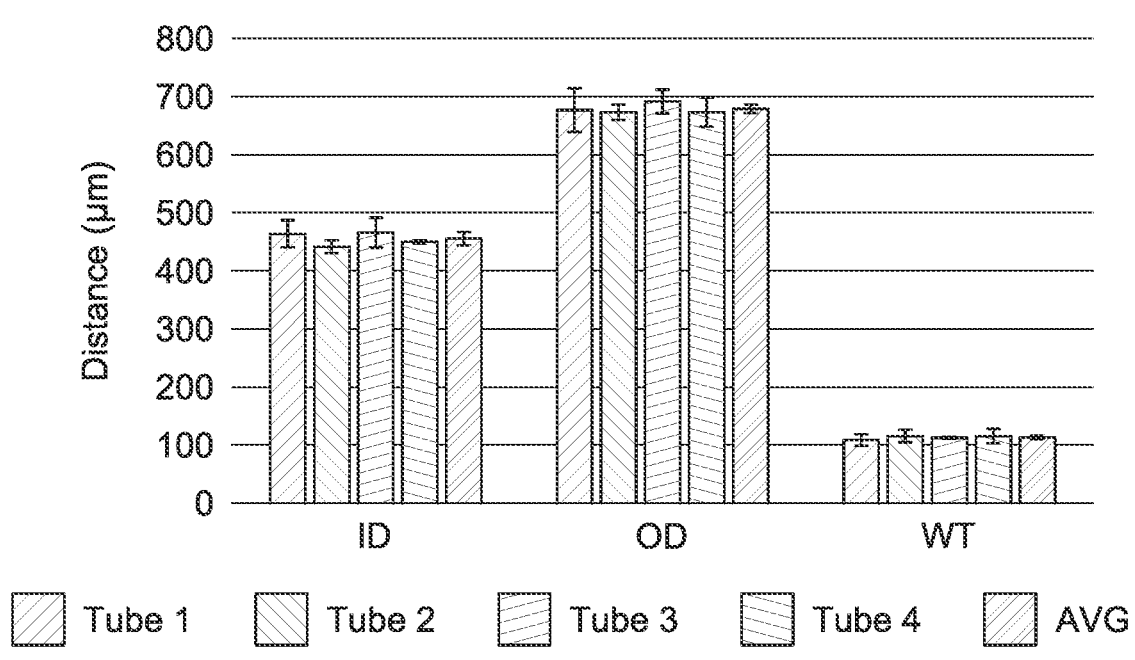
FIG. 11B is a chart illustrating alginate tube dimensions generated from a four-port planar extruder in accordance with example embodiments of the present disclosure.

Referring to FIG. 11B, results of the analysis of the 4-Port Planar extruder are shown. The standard deviations for the ID, OD, and WT are 10.1, 7.8, and 2.5 μm respectively. These results show that the planar extruder design can split flow more consistently than the radial design. It is also important to note that the crosslinking solution is flowed at 5,000 μL/min/port for the planar design and 10,000 μL/min/port for the radial design. This means that this reduction in standard deviation occurred in a region of higher sensitivity, a small change in flow ratio of the sheath to the alginate+ core resulting in larger changes of dimension. The range for the ID, OD, and WT are 24.2, 19.3, and 6.1 μm respectively.

The planar design reduces the range by 12.6, 31.9, and 6.4 μm for ID, OD, and WT when compared to the radial 4-Port design.

The effects of gravity can affect radial extruders in more possible variations than in planar extruders. The 4-Port Planar Extruder does not split flow directly 1 to 4, but rather as a stepped process from a 1 to 2 split and then 1 to 2 again to get 2 to 4. For the radial geometry, the extruder should be level to not have gravity play a role in splitting the flow. For example, if the extruder is tilted towards Tube 1, the stagnation plane (formed by the base 408) is tilted towards Tube 1 and more flow will be directed towards Tube 1. With the planar design, being level in one direction facilitates even splitting of the flow. True level of the planar design can provide for the tubes to have the hollow space be centered, which provides for a consistent wall thickness all the way around the hollow space.

Experimental data for the 8-Port Radial extruder showed the flow was not split evenly between all 8 tubes. The standard deviations for the ID, OD, and WT are 36.7, 29.8, and 7.8 μm respectively. The range of ID, OD, and WT are 132.9, 98.2, and 19.8 μm respectively. As more ports are added to a Radial branch portion, the more imprecisions in the construction or imprecise leveling of the extruder would affect the ability to evenly split between the ports.

Experimental data for the 8-Port Planar extruder showed more even splitting than from the 8-Port Radial design. In the 8-Port Planar extruder the flow was split from 1 to 2, then 2 to 4, and finally 4 to 8. Similar to the 4-Port Planar extruder, the flow rates of fluids are in a range where the same fluctuation results in larger changes in dimensions (e.g., lower flow rates than in the Radial designs). The tubes showed less dimensional variance than the 8-Port Radial extruder. This was quantitatively seen by the standard deviations for the ID, OD, and WT being 16.6, 21.6, and 7.6 μm respectively. This was a reduction in the standard deviation of 20.6, 8.2, and 0.2 μm for the ID, OD, and WT. The range for the 8-Port Planar extruder was 46.9, 80.7, and 21.6 μm for the ID, OD, and WT. This was a reduction of 86.0 and 17.5 μm for the ID and OD, while the range of the WT increased by 1.8 μm but still decreased the standard deviation by 0.2 μm. Only one tube of the eight tubes exhibited slightly smaller dimensions.

Example 2—Port Scaling and Tube Dimensions

Figure 12:
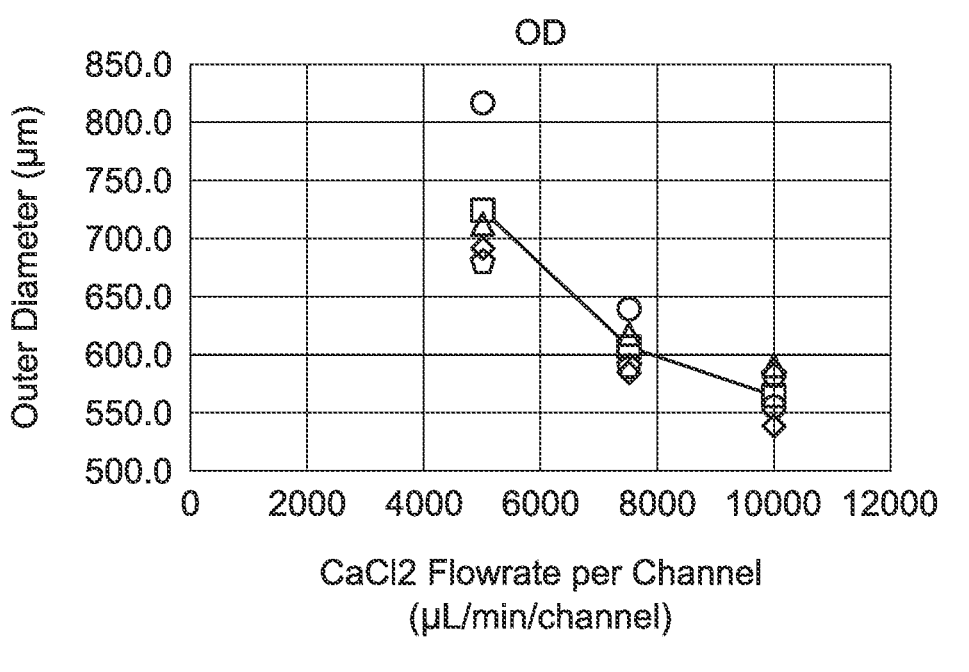
FIG. 12 is a chart illustrating alginate tube outer diameter lengths for extruders having various numbers of output ports over various flowrates of calcium chloride sheaths in accordance with example embodiments of the present disclosure.

Extruders 100 having differing output port numbers and radial branch portion configurations were analyzed to determine variations in physical dimensions of the individual tubes generated by individual output ports from the extruders 100 with equivalent output flow rates (e.g., scaled input flowrates based on number of outlet ports). The flowrates of the core (1.5% MethylCellulose (about 130 mPa*s)) and the shell (2.0% Alginate (about 570 mPa*s)), were kept constant at 40 μL/min/outlet port and 60 μL/min/outlet port, respectively. The flowrate of the sheath (100 mM CaCl2 (about 1 mPa*s)) was 5,000, 7,500, and 10,000 μL/min/port. Tubes were collected from a 1, 2, 4, and 8 port radial extruder. For multiport extruders, the tubes from every port were collected and imaged together. The inner diameter (ID), outer diameter (OD), and wall thickness (WT) were measured from pictures taken under a microscope. The WT was averaged from the two WT measurements of a microscope picture. For the single port extruder, 5 pictures where taken and measurements averaged, and for multiple port extruders 10 pictures were taken. FIG. 12 represents data results for the outer diameter for the extruders over the different sheath flowrates. The tube dimensions are shown as being maintained at the same or substantially similar dimensions for each port. Additionally, as the flow rate of the calcium chloride solution increased, the tube dimensions decreased, indicating that the ID, OD, and WT can be adjusted based on changes to the sheath flowrate.

Experiment 3—Flow Rate Scaling and Tube Dimensions

Figure 13:
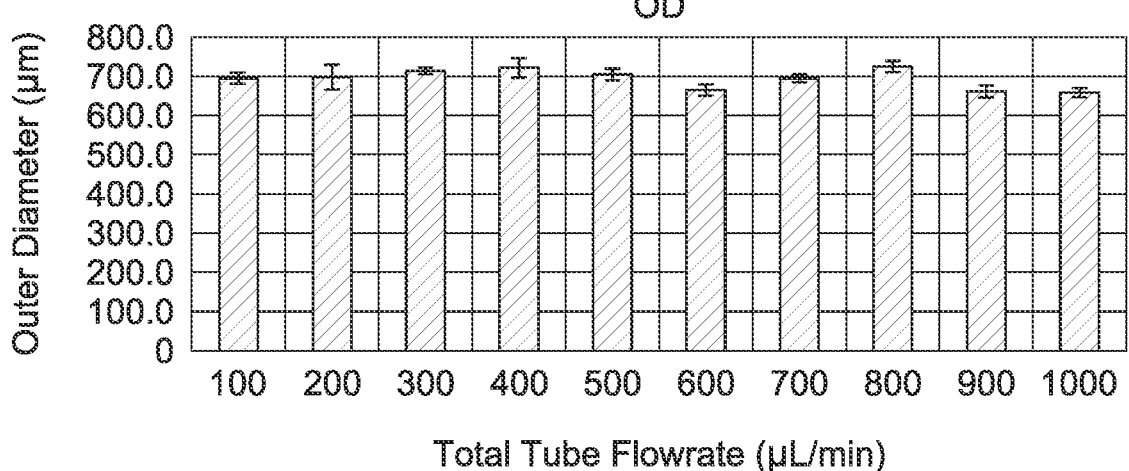
FIG. 13 is a chart illustrating alginate tube outer diameter lengths based on various extruder output flowrates.

Tri-axial single-port extruders were analyzed to determine how proportional increases in flow rates of the core solution, hydrogel solution, and crosslinking solution would affect tube dimensions. The flow rate ratio used was 40:60:5000 μL/min for the core solution (1.5% Methylcellulose (about 130 mPa*s)), the shell solution (2.0% Alginate (about 570 mPa*s)), and the cross-linking solution (100 mM $CaCl_2$) (about 1 mPa*s)), respectively. The tube flowrate (core and shell flows) was flown at 100 μL/min to 1000 μL/min with steps of 100 μL/min. From each condition a single tube was collected that encapsulated 100 μL of core solution. Each tube was imaged at least 5 times and the dimensions for ID, OD, and WT were averaged across those 5 images. FIG. 13 represents data results for the outer diameter for the extruders over the different tube flowrates. The standard deviation for the ID, OD, and WT are 12.0, 23.2, and 9.3 μm respectively. The data indicates that tube dimensions do not substantially change when the flow rates are less than 400:600:50000 μL/min for the Core: Shell: Sheath, and that the laminar flow structure is maintained. As long as the laminar flow structure is maintained, the flow rates could be scaled even higher and tube dimensions remain consistent.

Experiment 4—Fluid Viscosity and Tube Dimensions

Tri-axial single-port extruders were analyzed to determine how increases in the viscosity of the crosslinking solution would affect tube dimensions. Experiments demonstrated that the sheath flow exerts a shear force on the alginate/core flows, because increasing the sheath flow, the shear increases and the tube becomes thinner (for example, shown in FIG. 12). However, the shear force does not only depend on the flow rate of the sheath, but also on its viscosity, where higher viscosities would cause more shear to be exerted on the tube, and effective tube modulation can be accomplished at lower calcium chloride flow rates. Experiments were performed to determine the effects of increasing the viscosity of the sheath flow on the tube dimensions. The calcium chloride cross-linking fluid was tested under control conditions (no viscosity adjustment) and by adjusting viscosity through addition of methylcellulose in a 0.25% and 0.5% (w/v) concentration. The viscosity of control calcium chloride (100 mM $CaCl_2$)) is almost the same as the viscosity of water (e.g., 1 mPa*s), while being modified with a 0.25% or a 0.50% concentration results in viscosities of about 5 mPa*s and about 10 mPa*s, respectively. The flow rates of the core and shell were kept constant at 40 μL/min and 60 μL/min, respectively.

Figure 14:
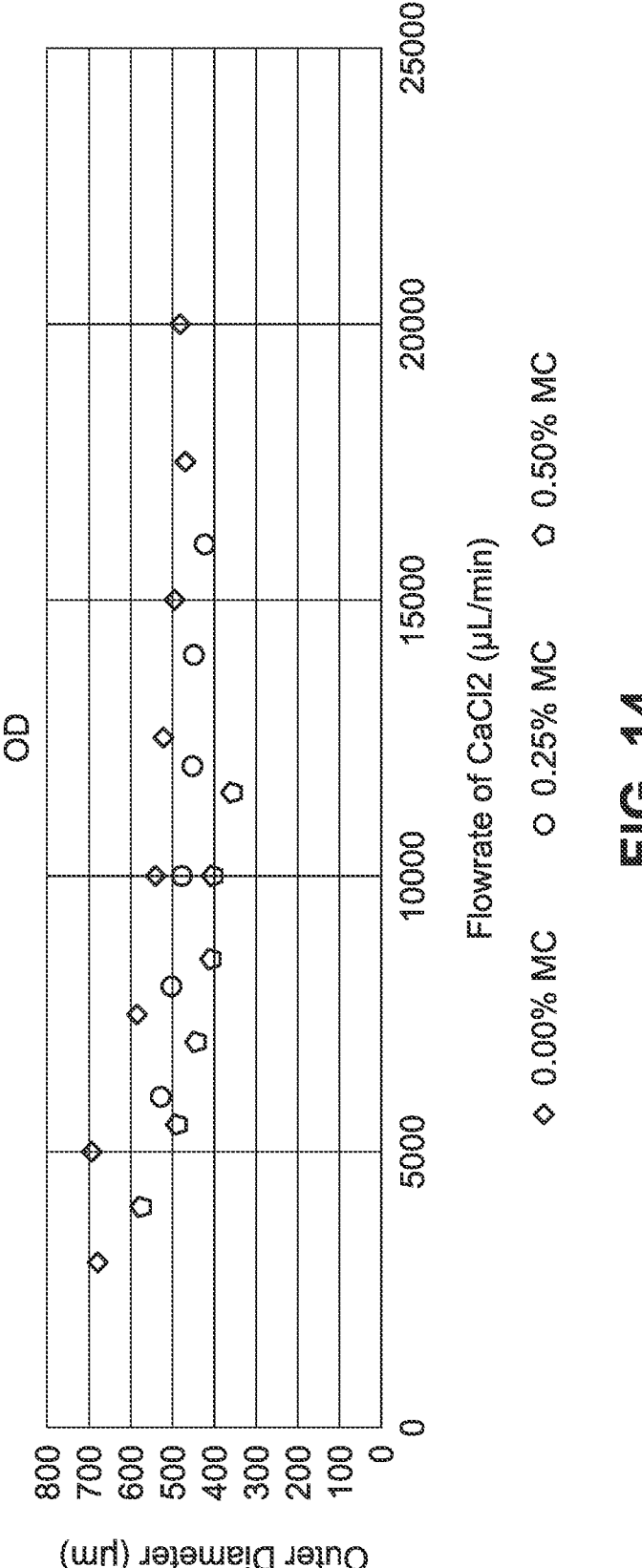
FIG. 14 is a chart illustrating alginate tube outer diameter lengths based on differing calcium chloride viscosities with various compositions of calcium chloride and methylcellulose.

FIG. 14 represents data results for the outer diameter for the extruders over the different cross-linking flowrates and viscosities (based on methylcellulose composition). The results show that as the viscosity of the sheath flow increases at the same flow rate, the tube OD becomes smaller. The change in tube dimensions becomes smaller as the sheath flow increases and a plateau is reached. For example, at 10,000 μL/min the unmodified $CaCl_2$) produced a tube with an outer diameter of about 540 μm. When the sheath flow viscosity was changed to about 5 mPa*s, the OD was about 480 μm, (a reduction in OD of about 11%). To achieve this reduction in tube OD with unmodified $CaCl_2$), the flow rate would be about 17,500 μL/min. If the viscosity of the sheath flow is increased to about 10 mPa*s, an OD of about 400 μm is found, (a reduction in OD of about 26% compared to unmodified). In order to achieve this (OD of about 400 μm) with unmodified $CaCl_2$), the flow rate would be more than 20,000 μL/min. To achieve this with a 5 mPa*s $CaCl_2$) solution, the flow rate would be about 17500 μL/min.

Additional viscosity experiments were performed using a tri-axial two-port extruder 100 and unmodified and modified calcium chloride (e.g., 0.0% methylcellulose 100 mM $CaCl_2$) and 0.25% methylcellulose 100 mM $CaCl_2$) (about 5 mPa*s), respectively. The core and shell were kept at the same flow rates of 40 μL/min/port and 60 μL/min/port, respectively. The results illustrated similar trends as with the experiments involving the single port extruder described with respect to FIG. 14.

Additional viscosity experiments were performed that modified the viscosity of the cell solution and the hydrogel solution. For example, experiments using no added methylcellulose in the cell solution demonstrated changes in tube dimension as compared to 1.5% w/v methylcellulose, where under the same flow conditions, a cell solution containing no methylcellulose (about 1 mPa*s) has a smaller core in the tube than one with 1.5% methylcellulose (about 130 mPa*s). Experiments using different amounts of alginate demonstrated changes in tube dimension due to varying viscosity of the alginate (e.g., about 250 mPa*s for a 1.5% alginate solution; about 570 mPa*s for a 2% alginate solution), where under the same flow conditions, tubes using lower amounts of alginate result in thinner tubes (e.g., due to the calcium chloride pushing at the same force, but the lower viscosity of the alginate provides less resistance to the pressure).

CONCLUSION

Unless otherwise stipulated or if context dictates otherwise, percentages provided herein with respect to fluids are expressed as % weight per volume (% w/v).

It will be appreciated that features described herein with respect to embodiments or implementations can be combined with any other feature or features described with respect to the same or alternative embodiments, unless context otherwise dictates, without departing from the scope of the present disclosure.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

The invention claimed is:

1. A multi-axial multi-port extruder comprising
a plurality of input ports coupled with an extruder body, the extruder body defining a plurality of fluid channels, wherein each fluid channel is fluidically coupled with a respective one of the plurality of input ports, the extruder body further defining a plurality of branch portions including a plurality of branches extending from each fluid channel of the plurality of fluid channels, wherein each branch portion of the plurality of branch portions includes a planar branch portion including a first channel split into two sub-channels having substantially the same internal dimension and each of the two sub-channels includes a second channel split into two additional sub-channels having substantially the same internal dimension;
a plurality of outlet ports fluidically coupled with the plurality of branches, wherein one more than the number of planar branch portions extending from one fluid channel is equal to the number of outlet ports in the plurality of outlet ports to fluidically couple each input port of the plurality of input ports with each outlet port of the plurality of outlet ports; and
a fluid chamber fluidically coupled with a substantially vertical fluid channel of the plurality of fluid channels and with an angled channel that is fluidically coupled with a different input port than the substantially vertical fluid channel, the fluid chamber defining a first chamber portion with a separating wall that physically separates the substantially vertical fluid channel from the first chamber portion, the angled channel coupled with the first chamber portion at an intersection that includes a fillet feature, at least a portion of the fillet feature extending above a top of the separating wall, the fluid chamber configured to introduce a first stream of fluid from the angled channel into the first chamber portion and around a second stream of fluid in the substantially vertical fluid channel, wherein the separating wall terminates at a bottom of the fluid chamber to permit contact between the first stream of fluid and the second stream of fluid as a co-axial fluid stream.

2. The multi-axial multi-port extruder of claim 1, wherein the plurality of input ports includes three input ports to provide a tri-axial arrangement of internal fluid flows.

3. The multi-axial multi-port extruder of claim 1, wherein the first chamber portion of the fluid chamber is an annular chamber defined between the extruder body and the separating wall.

4. The multi-axial multi-port extruder of claim 3, wherein the angled channel is coupled with a top of the annular chamber.

5. The multi-axial multi-port extruder of claim 1, wherein a cross-sectional area of one fluid channel is substantially equal to a sum of each cross-sectional area of each branch extending from the one fluid channel.

6. The multi-axial multi-port extruder of claim 1, further comprising a second fluid chamber fluidically coupled with the fluid chamber to receive the co-axial fluid stream and with a second angled channel that is fluidically coupled with a different input port than each of the substantially vertical fluid channel and the angled channel.

7. The multi-axial multi-port extruder of claim 6, wherein the second fluid chamber defining an initial chamber portion with a second separating wall that physically separates the initial chamber portion from a fluid channel coupled between fluid chamber and the second fluid chamber, the second angled channel coupled with the initial chamber portion, the second fluid chamber configured to introduce a third stream of fluid from the second angled channel into the initial chamber portion and around the co-axial fluid stream in the fluid channel coupled between fluid chamber and the second fluid chamber.

8. The multi-axial multi-port extruder of claim 7, wherein the second separating wall terminates at a bottom of the second fluid chamber to permit contact between the co-axial fluid stream and the third stream of fluid as a tri-axial fluid stream.

9. The multi-axial multi-port extruder of claim 8, wherein the second fluid chamber further includes a second chamber portion beneath and fluidically coupled with the initial chamber portion, the second chamber portion having an inwardly tapering outer wall, and wherein the second angled channel intersects with the initial chamber portion.

10. A multi-axial multi-port extruder comprising a plurality of input ports coupled with an extruder body, the extruder body defining a plurality of fluid channels, wherein each fluid channel is fluidically coupled with a respective one of the plurality of input ports, the extruder body further defining a plurality of branch portions including a plurality of branches extending from each fluid channel of the plurality of fluid channels, wherein each branch portion of the plurality of branch portions includes a planar branch portion including a first channel split into two sub-channels having substantially the same internal dimension and each of the two sub-channels includes a second channel split into two additional sub-channels having substantially the same internal dimension;

a plurality of outlet ports fluidically coupled with the plurality of branches, wherein one more than the number of planar branch portions extending from one fluid channel is equal to the number of outlet ports in the plurality of outlet ports to fluidically couple each input port of the plurality of input ports with each outlet port of the plurality of outlet ports; and a fluid chamber fluidically coupled with a substantially vertical fluid channel of the plurality of fluid channels and with an angled channel that is fluidically coupled with a different input port than the substantially vertical fluid channel, the fluid chamber defining a first chamber portion with a separating wall that physically separates the substantially vertical fluid channel from the first chamber portion, wherein the first chamber portion is an annular chamber defined between the extruder body and the separating wall, and wherein the angled channel coupled with the first chamber portion at an angle from horizontal from 30 degrees to 60 degrees and at an intersection that includes a fillet feature, at least a portion of the fillet feature extending above a top of the separating wall, the fluid chamber configured to introduce a first stream of fluid from the angled channel into the first chamber portion and around a second stream of fluid in the substantially vertical fluid channel, wherein the separating wall terminates at a bottom of the fluid chamber to permit contact between the first stream of fluid and the second stream of fluid as a co-axial fluid stream.

11. A method for simultaneously generating multiple hydrogel tubes containing a core of cell solution utilizing a multi-axial multi-port extruder, the method comprising:

introducing a hydrogel solution and a cell solution to individual input ports of a multi-axial multi-port extruder, the multi-axial multi-port extruder including:

a plurality of input ports coupled with an extruder body, the extruder body defining a plurality of fluid channels, wherein each fluid channel is fluidically coupled with a respective one of the plurality of input ports, the extruder body further defining a plurality of branch portions including a plurality of branches extending from each fluid channel of the plurality of fluid channels, wherein each branch portion of the plurality of branch portions includes a planar branch portion including a first channel split into two sub-channels having substantially the same internal dimension and each of the two sub-channels includes a second channel split into two additional sub-channels having substantially the same internal dimension;

a plurality of outlet ports fluidically coupled with the plurality of branches, wherein one more than the number of planar branch portions extending from one fluid channel is equal to the number of outlet ports in the plurality of outlet ports to fluidically couple each input port of the plurality of input ports with each outlet port of the plurality of outlet ports; and a fluid chamber fluidically coupled with a substantially vertical fluid channel of the plurality of fluid channels and with an angled channel that is fluidically coupled with a different input port than the substantially vertical fluid channel, the fluid chamber defining a first chamber portion with a separating wall that physically separates the substantially vertical fluid channel from the first chamber portion, the angled channel coupled with the first chamber portion at an intersection that includes a fillet feature, at least a portion of the fillet feature extending above a top of the separating wall, the fluid chamber configured to introduce a stream of the hydrogel solution from the angled channel into the first chamber portion and around a stream of the cell solution in the substantially vertical fluid channel, wherein the separating wall terminates at a bottom of the fluid chamber to permit contact between the stream of the hydrogel solution and the stream of the cell solution as a co-axial fluid stream with the cell solution as a core; and introducing the co-axial fluid stream to a cross-linking solution to form hydrogel tubes.

12. The method of claim 11, wherein the cross-linking solution is introduced to the multi-axial multi-port extruder for introduction to the co-axial fluid stream.

13. The method of claim 12, further comprising:

adjusting at least one dimension of each hydrogel tube through adjusting a flow rate of one or more of the hydrogel solution, the cell solution, and the cross-linking solution to the multi-axial multi-port extruder.

14. The method of claim 12, further comprising:

adjusting at least one dimension of each hydrogel tube through adjusting a viscosity of at least one of the hydrogel solution, the cell solution, or the cross-linking solution introduced to the multi-axial multi-port extruder.

15. The method of claim 11, wherein the cross-linking solution is positioned beneath the multi-axial multi-port extruder to receive the co-axial fluid stream.

16. The method of claim 11, further comprising:

adjusting at least one dimension of each hydrogel tube through adjusting a flow rate of one or more of the hydrogel solution and the cell solution to the multi-axial multi-port extruder.

* * * * *